United States Patent
Jang et al.

(10) Patent No.: US 10,119,074 B2
(45) Date of Patent: Nov. 6, 2018

(54) LIQUID CRYSTAL COMPOSITION AND DISPLAY DEVICE INCLUDING THE SAME

(71) Applicant: SAMSUNG DISPLAY CO., LTD., Yongin-si, Gyeonggi-do (KR)

(72) Inventors: Ji Eun Jang, Suwon-si (KR); Sun Young Kwon, Seoul (KR); Tae Hoon Kim, Suwon-si (KR); Jong Ho Son, Seoul (KR); Keun Chan Oh, Hwaseong-si (KR); Won Gap Yoon, Suwon-si (KR); Gak Seok Lee, Hwaseong-si (KR); Jin Hyeong Lee, Hwaseong-si (KR); Chang Hun Lee, Hwaseong-si (KR)

(73) Assignee: SAMSUNG DISPLAY CO., LTD., Gyeonggi-Do (KR)

( * ) Notice: Subject to any disclaimer, the term of this patent is extended or adjusted under 35 U.S.C. 154(b) by 0 days.

(21) Appl. No.: 15/421,848

(22) Filed: Feb. 1, 2017

(65) Prior Publication Data
US 2018/0086981 A1    Mar. 29, 2018

(30) Foreign Application Priority Data
Sep. 27, 2016    (KR) .................. 10-2016-0123995

(51) Int. Cl.
| | | |
|---|---|---|
| G02F 1/1333 | (2006.01) | |
| C09K 19/34 | (2006.01) | |
| C07D 307/83 | (2006.01) | |
| G02F 1/1337 | (2006.01) | |
| G02F 1/1343 | (2006.01) | |

(52) U.S. Cl.
CPC ........ *C09K 19/3405* (2013.01); *C07D 307/83* (2013.01); *G02F 1/133723* (2013.01); *G02F 1/134309* (2013.01); *C09K 2019/3408* (2013.01); *G02F 2202/023* (2013.01)

(58) Field of Classification Search
CPC ........ C09K 19/3405; C09K 2019/3408; G02F 1/1333; G02F 1/133723; G02F 1/134309; G02F 2202/023; C07D 307/83
USPC .................................................. 252/299.61
See application file for complete search history.

(56) References Cited

U.S. PATENT DOCUMENTS

| | | |
|---|---|---|
| 7,122,228 B2 | 10/2006 | Reiffenrath et al. |
| 7,169,449 B2 | 1/2007 | Nakanishi et al. |
| 7,714,977 B2 | 5/2010 | Hotaka et al. |
| 7,731,865 B2 | 6/2010 | Bernatz et al. |
| 7,807,068 B2 | 10/2010 | Bremer et al. |
| 8,114,310 B2 | 2/2012 | Bernatz et al. |
| 8,304,035 B2 | 11/2012 | Bernatz et al. |

(Continued)

FOREIGN PATENT DOCUMENTS

| | | |
|---|---|---|
| CN | 100415730 | 9/2008 |
| CN | 103969863 | 8/2014 |

(Continued)

*Primary Examiner* — Geraldina Visconti
(74) *Attorney, Agent, or Firm* — Cantor Colburn LLP

(57) ABSTRACT

A liquid crystal composition includes a compound having a structure represented by formula A-1:

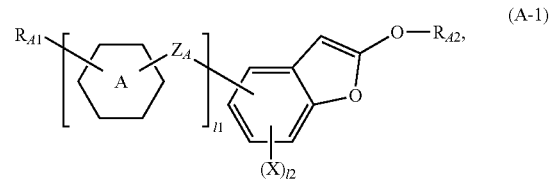

wherein

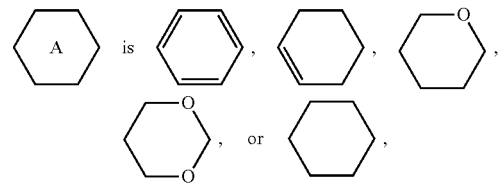

$R_{A1}$ is an alkyl group, an alkoxy group, a cyano group, a halogen atom, or a hydrogen atom, $R_{A2}$ is an alkyl group, a cyano group, a halogen atom, or a hydrogen atom, $Z_A$ is *—O—*, *—COO—*, *—OCO—*, *—CF$_2$O—*, *—OCF$_2$—*, *—CH$_2$O—*, *—OCH$_2$—*, *—SCH$_2$—*, *—CH$_2$S—*, *—C$_2$F$_4$—*, *—CH$_2$CF$_2$—*, *—CF$_2$CH$_2$—*, *—(CH$_2$)$_k$—*, *—CH=CH—*, *—CF=CF—*, *—CH=CF—*, *—CF=CH—*, *—C≡C—*, *—CH=CHCH$_2$O—*, or a single bond, X is a halogen atom, each of l1 and l2 is independently an integer of 0 to 2, and when l1 is 2

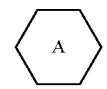

and $Z_A$ in a repeating unit defined by l1 are the same or different, wherein k is an integer of 1 to 5 and "*" indicates a point of attachment.

20 Claims, 5 Drawing Sheets

(56) References Cited

U.S. PATENT DOCUMENTS

| | | |
|---|---|---|
| 8,313,669 B2 | 11/2012 | Bernatz et al. |
| 8,697,200 B2 | 4/2014 | Goetz et al. |
| 8,765,013 B2 | 7/2014 | Kurisawa et al. |
| 8,940,375 B2 | 1/2015 | Bremer et al. |
| 8,968,842 B2 | 3/2015 | Bae et al. |
| 8,999,459 B2 | 4/2015 | Bernatz et al. |
| 9,005,720 B2 | 4/2015 | Goetz et al. |
| 9,181,481 B2 | 11/2015 | Bae et al. |
| 9,181,482 B2 | 11/2015 | Goetz et al. |
| 2017/0038642 A1 | 2/2017 | Bae et al. |
| 2017/0052412 A1 | 2/2017 | Bae et al. |
| 2017/0292074 A1* | 10/2017 | Bae .................... C07D 307/80 |

FOREIGN PATENT DOCUMENTS

| | | |
|---|---|---|
| CN | 106468839 A | 3/2017 |
| DE | 19909760 | 10/1999 |
| DE | 19909761 A1 | 10/1999 |
| JP | 2003509507 A | 3/2003 |
| JP | 2014142585 A | 8/2014 |
| KR | 100884117 B1 | 2/2009 |
| KR | 1020100070337 A | 6/2010 |
| KR | 1020110002039 A | 1/2011 |
| KR | 1020140095326 A | 8/2014 |
| KR | 1020170016541 A | 2/2017 |
| KR | 1020170021940 A | 3/2017 |
| WO | 0121606 A1 | 3/2001 |
| WO | 03010120 A1 | 2/2003 |
| WO | 2009030322 A1 | 3/2009 |
| WO | 2009118086 A1 | 10/2009 |

* cited by examiner

LIQUID CRYSTAL COMPOSITION AND DISPLAY DEVICE INCLUDING THE SAME

This application claims priority to Korean Patent Application No. 10-2016-0123995, filed on Sep. 27, 2016 in the Korean Intellectual Property Office, and all the benefits accruing therefrom under 35 U.S.C. § 119, the disclosure of which in its entirety is herein incorporated by reference

BACKGROUND

1. Field

The present disclosure relates to a liquid crystal composition and a display device including the same.

2. Description of the Related Art

A liquid crystal display (LCDs) is a widely used type of flat panel display. Generally, an LCD includes a pair of substrates having field generating electrodes, such as pixel electrodes and a common electrode, and a liquid crystal layer interposed between the two substrates. In an LCD, voltages are applied to the field generating electrodes to determine the alignment direction of liquid crystals in the liquid crystal layer and to control polarization of incident light. As a result, a desired image is displayed on the LCD.

As the use of LCDs becomes more diversified, increased response speed, increased contrast, and decreased driving voltages are advantageous. To improve these properties, it is desirable to develop a liquid crystal material having low rotational viscosity, high chemical and physical stability, appropriate elastic modulus, and superior refractive index anisotropy and dielectric anisotropy.

SUMMARY

Aspects of the present disclosure provide a liquid crystal composition having high physical and chemical stability and low rotational viscosity.

Aspects of the present disclosure also provide a display device having improved response speed, improved contrast, and a low driving voltage.

According to an exemplary embodiment, a liquid crystal composition includes a compound having a structure represented by formula A-1:

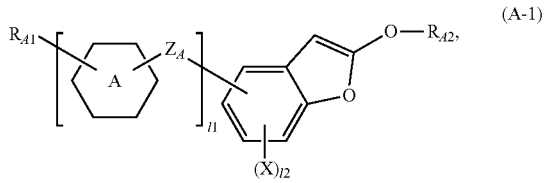

(A-1)

wherein

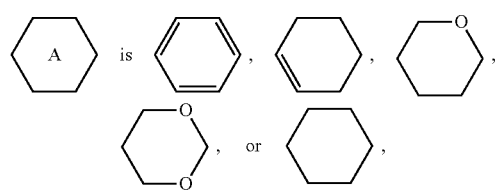

$R_{A1}$ is an alkyl group, an alkoxy group, a cyano group, a halogen atom, or a hydrogen atom, $R_{A2}$ is an alkyl group, a cyano group, a halogen atom, or a hydrogen atom, $Z_A$ is *—O—*, *—COO—*, *—OCO—*, *—CF$_2$O—*, *—OCF$_2$—*, *—CH$_2$O—*, *—OCH$_2$—*, *—SCH$_2$—*, *—CH$_2$S—*, *—C$_2$F$_4$—*, *—CH$_2$CF$_2$—*, *—CF$_2$CH$_2$—*, *—(CH$_2$)$_k$—*, *—CH=CH—*, *—CF=CF—*, *—CH=CF—*, *—CF=CH—*, *—C≡C—*, *—CH=CHCH$_2$O—*, or a single bond, X is a halogen atom, each of l1 and l2 is independently an integer of 0 to 2, and when l1 is 2

and $Z_A$ in a repeating unit defined by l1 are the same or different, k is an integer of 1 to 5, and "*" indicates a point of attachment.

In an exemplary embodiment, the compound having the structure represented by formula A-1 may be a compound having a structure represented by formula A-2:

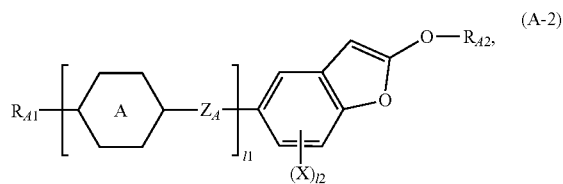

(A-2)

wherein

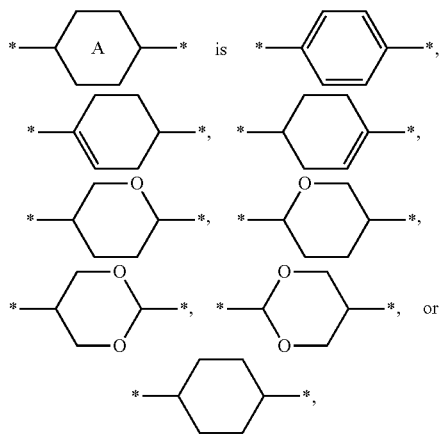

$R_{A1}$ is an alkyl group having a carbon number of 1 to 5, an alkoxy group having a carbon number of 1 to 5, a cyano group, a halogen atom, or a hydrogen atom, $R_{A2}$ is an alkyl group having a carbon number of 1 to 5, a cyano group, a halogen atom, or a hydrogen atom, and $Z_A$, X, l1, and l2 are the same as those in formula A-1.

In an exemplary embodiment, the compound having the structure represented by formula A-2 may be a compound having a structure represented by formula A-3, formula A-4, or formula A-5:

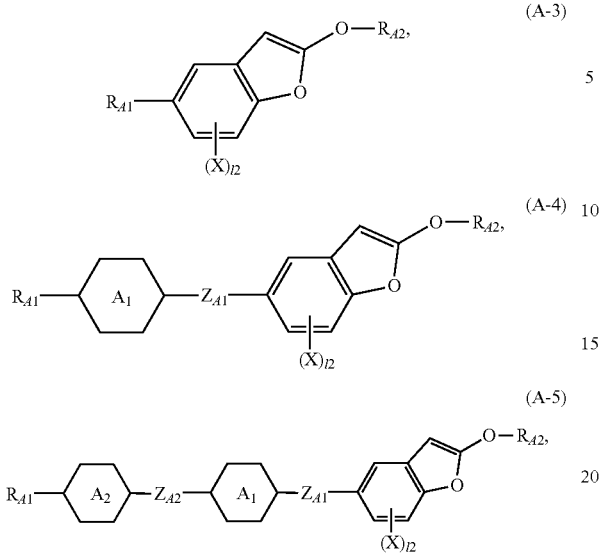

wherein each of

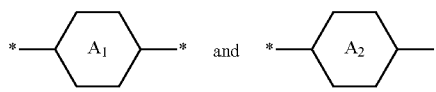

is independently,

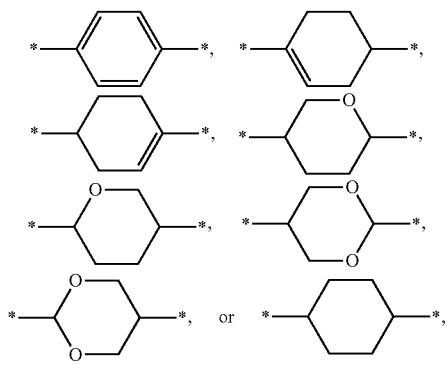

each of $Z_{A1}$ and $Z_{A2}$ is independently *—O—*, *—COO—*, *—OCO—*, *—CF$_2$O—*, *—OCF$_2$—*, *—CH$_2$O—*, *—OCH$_2$—*, *—SCH$_2$—*, *—CH$_2$S—*, *—C$_2$F$_4$—*, *—CH$_2$CF$_2$—*, *—CF$_2$CH$_2$—*, *—(CH$_2$)$_k$—*, *—CH=CH—*, *—CF=CF—*, *—CH=CF—*, *—CF=CH—*, *—C≡C—*, *—CH=CHCH$_2$O—*, or a single bond, $R_{A1}$, $R_{A2}$, X, and l2 are the same as those in formula A-2, and k is an integer of 1 to 5.

In an exemplary embodiment, the compound having the structure represented by formula A-3, formula A-4, or formula A-5 may be a compound having a structure represented by any one of formulas A-6 to A-13:

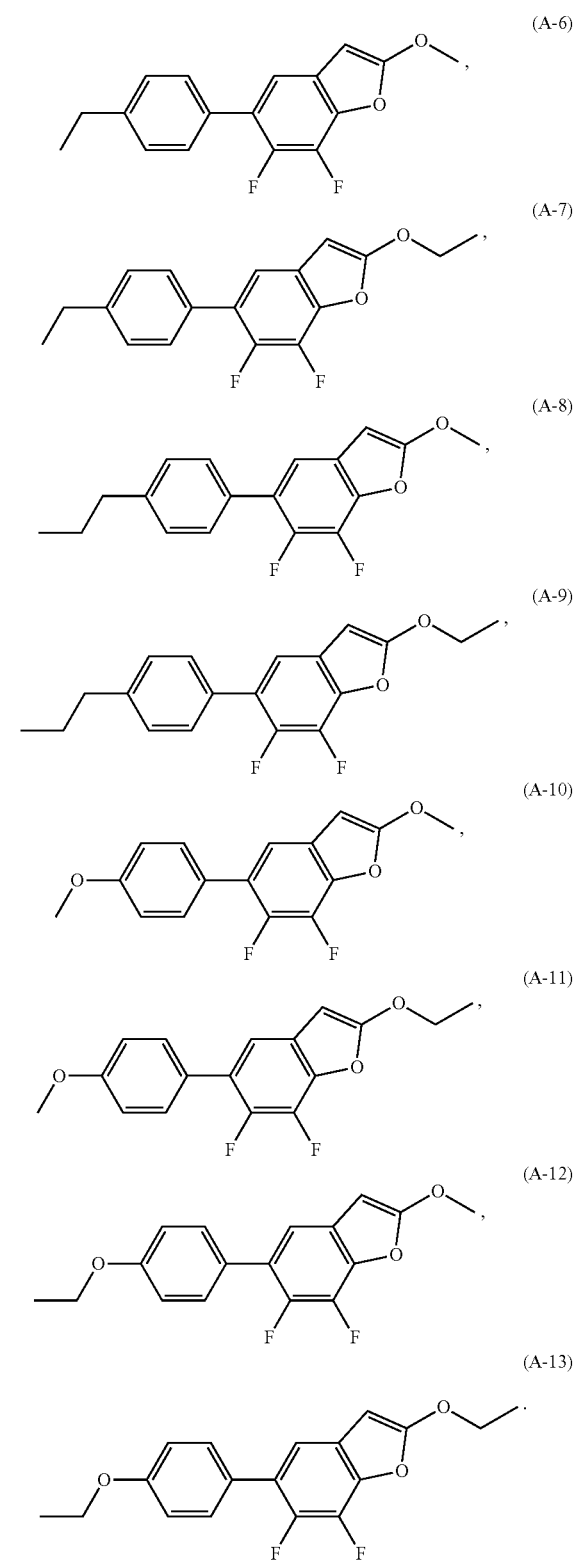

In an exemplary embodiment, the liquid crystal composition includes one or more of the compounds having the structures represented by formulas A-6 to A-13.

In an exemplary embodiment, the compound having the structure represented by any one of formulas A-6 to A-13 may have a refractive index anisotropy of about 0.230 to about 0.260 and a rotational viscosity at 20° C. ($\gamma$ 1, 20° C.) of about 70 to about 100 millipascal-seconds (mPas).

In an exemplary embodiment, the liquid crystal composition may have a refractive index anisotropy of about 0.080 to about 0.120, a dielectric anisotropy of about −5.5 to about −2.8, and a rotational viscosity at 20° C. ($\gamma$ 1, 20° C.) of about 70 to about 110 mPas.

In an exemplary embodiment, the liquid crystal composition may further include a compound having a structure represented by formula B-1:

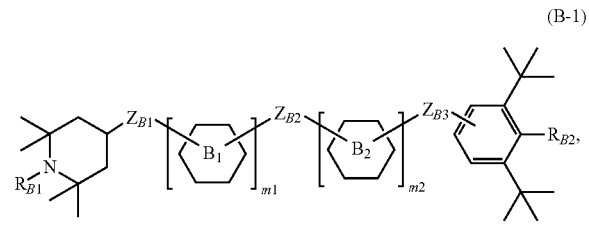

(B-1)

wherein each of

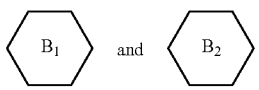

is independently

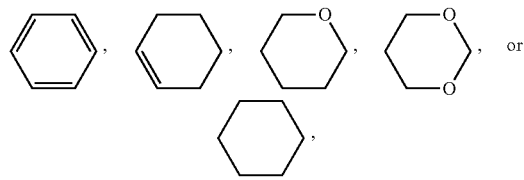

$R_{B1}$ is an alkyl group, an alkoxy group, or a hydrogen atom, $R_{B2}$ is an alkyl group, an alkoxy group, an acetamide group (—NHCOCH$_3$), a hydroxyl group (—OH), or a hydrogen atom, each of $Z_{B1}$, $Z_{B2}$, and $Z_{B3}$ is independently an alkylene group having a carbon number of 1 to 5, an alkenylene group having a carbon number of 2 to 3, *—O—*, *—COO—*, *—OCO—*, *—CF$_2$O—*, *—OCF$_2$—*, a single bond, or a double bond, and each of m1 and m2 is independently 0 or 1.

In an exemplary embodiment, the compound having the structure represented by formula B-1 may be a compound having a structure represented by formula B-2:

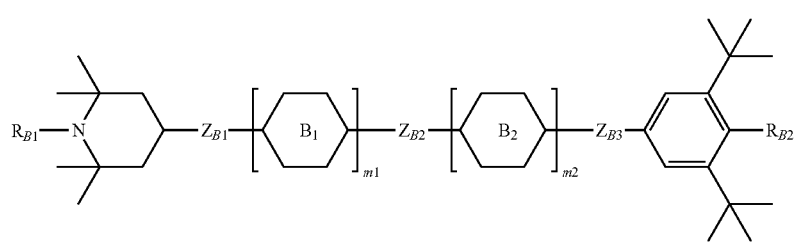

(B-2)

wherein each of

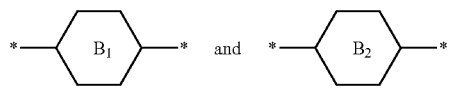

and is independently

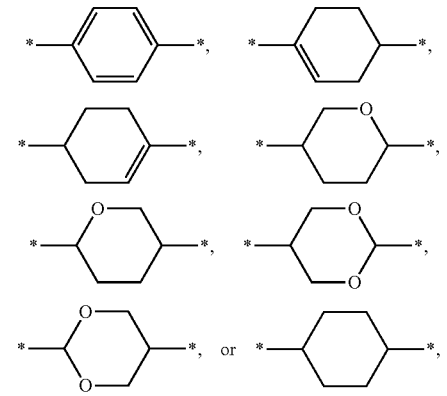

$R_{B1}$ is an alkyl group having a carbon number of 1 to 5, an alkoxy group having a carbon number of 1 to 5, or a hydrogen atom, $R_{B2}$ is an alkyl group having a carbon number of 1 to 4, an alkoxy group having a carbon number of 1 to 4, an acetamide group, a hydroxyl group, or a hydrogen atom, and $Z_{B1}$, $Z_{B2}$, $Z_{B3}$, m1, and m2 are the same as those in formula B-1.

In an exemplary embodiment, the compound having the structure represented by formula B-2 may be a compound having a structure represented by formula B-3, formula B-4, or formula B-5:

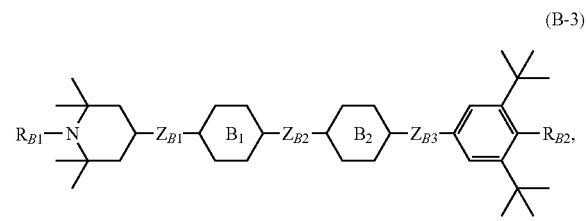

(B-3)

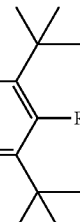

-continued (B-4)

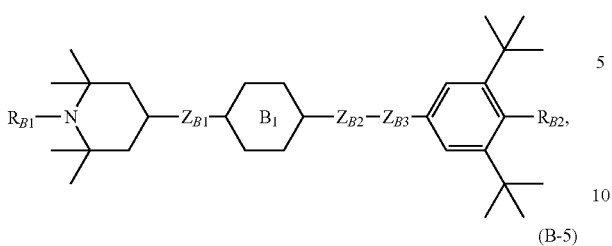

(B-5)

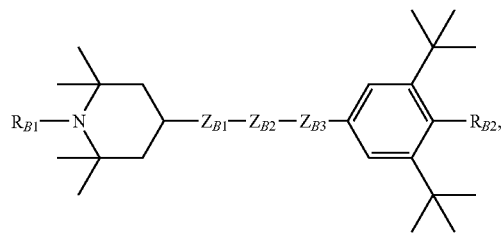

wherein

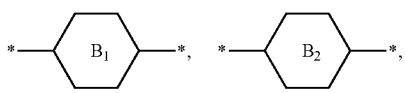

$R_{B1}$, $R_{B2}$, $Z_{B1}$, $Z_{B2}$, and $Z_{B3}$ are the same as those in formula B-2.

In an exemplary embodiment, the compound having the structure represented by formula B-3, formula B-4, or formula B-5 may be a compound having a structure represented by any one of formulas B-6 through B-9:

(B-6)

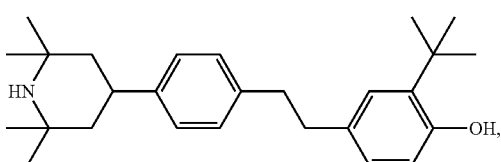

(B-7)

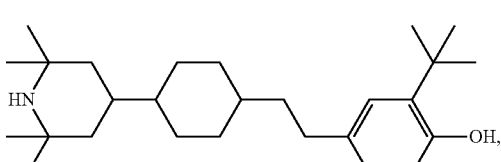

(B-8)

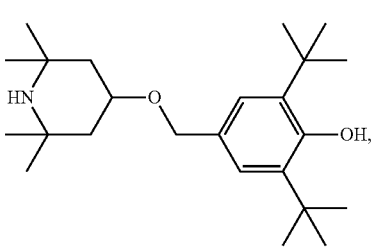

(B-9)

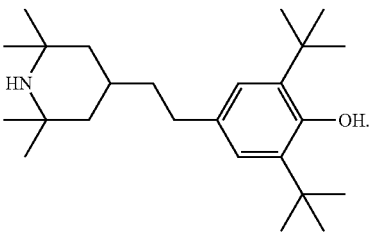

In an exemplary embodiment, the liquid crystal composition may further include a compound having a structure represented by formula C-1:

(C-1)

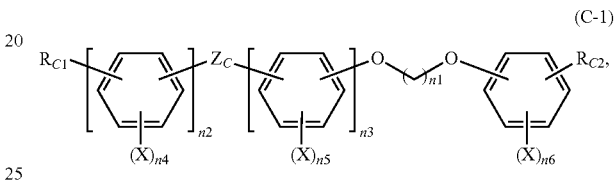

wherein each of $R_{C1}$ and $R_{C2}$ is independently

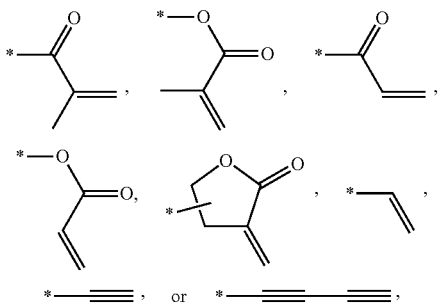

$Z_C$ is an alkylene group, an alkyleneoxy group, an ether group or a single bond, X is a halogen atom, n1 is an integer of 2 to 4, each of n2 and n3 is independently 0 or 1, and each of n4 to n6 is independently an integer of 0 to 2.

In an exemplary embodiment, the compound having the structure represented by formula C-1 may be a compound having a structure represented by formula C-2:

(C-2)

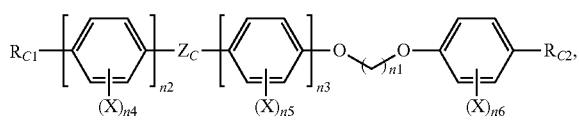

wherein $R_{C1}$, $R_{C2}$, $Z_C$, X, and n1 to n6 are the same as those in formula C-1.

In an exemplary embodiment, the compound having the structure represented by formula C-2 may be a compound having a structure represented by formula C-3 or formula C-4:

(C-3)
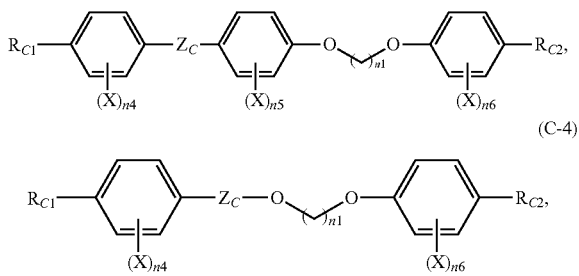

(C-4)

wherein $R_{C1}$, $R_{C2}$, $Z_C$, X, n1, n4, and n6 are the same as those in formula C-1.

In an exemplary embodiment, the compound having the structure represented by formula C-3 or formula C-4 may be a compound having a structure represented by any one of formulas C-5 to C-8:

(C-5)
(C-6)
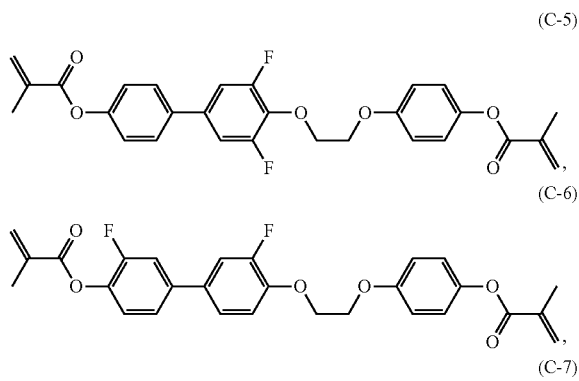

(C-7)
(C-8)
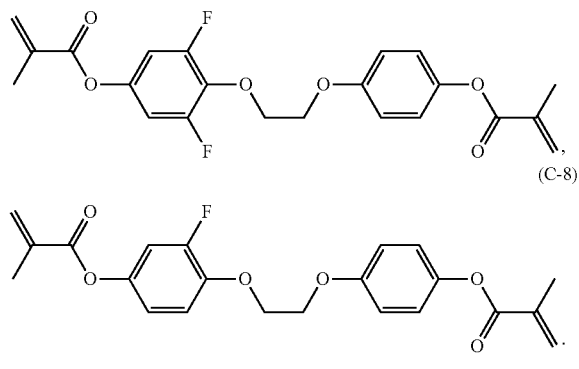

According to an exemplary embodiment, a display device includes: an insulating substrate; and a liquid crystal layer disposed on the insulating substrate and including a compound having a structure represented by formula A-1:

(A-1)
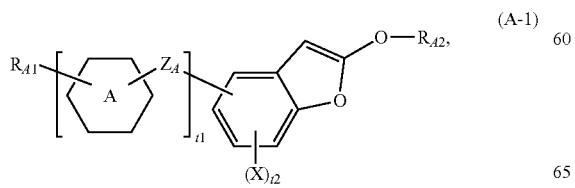

wherein

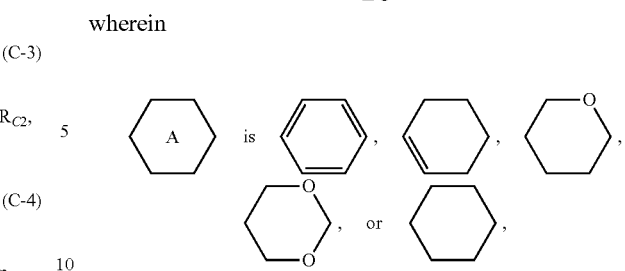

$R_{A1}$ is an alkyl group, an alkoxy group, a cyano group, a halogen atom, or a hydrogen atom, $R_{A2}$ is an alkyl group, a cyano group, a halogen atom, or a hydrogen atom, $Z_A$ is *—O—*, *—COO—*, *—OCO—*, *—CF$_2$O—*, *—OCF$_2$—*, *—CH$_2$O—*, *—OCH$_2$—*, *—SCH$_2$—*, *—CH$_2$S—*, *—C$_2$F$_4$—*, *—CH$_2$CF$_2$—*, *—CF$_2$CH$_2$—*, *—(CH$_2$)$_k$—*, *—CH═CH—*, *—CF═CF—*, *—CH═CF—*, *—CF═CH—*, *—C≡C—*, *—CH═CHCH$_2$O—*, or a single bond, X is a halogen atom, l1 is an integer of 0 to 2, l2 is an integer of 0 to 3, and when l1 is 2

and $Z_A$ in a repeating unit defined by l1 are the same or different, k is an integer of 1 to 5, and "*" indicates a point of attachment.

In an exemplary embodiment, the liquid crystal layer may further include a compound having a structure represented by formula B-1:

(B-1)
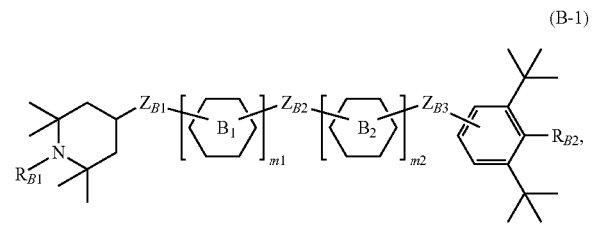

wherein each of

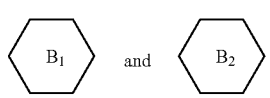

is independently

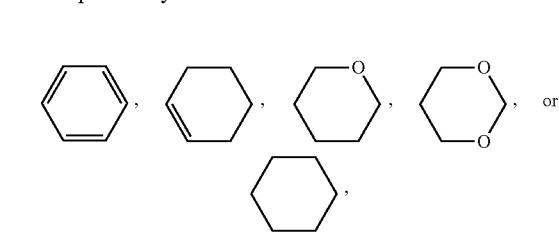

$R_{B1}$ is an alkyl group, an alkoxy group, or a hydrogen atom, $R_{B2}$ is an alkyl group, an alkoxy group, an acetamide group (—NHCOCH$_3$), a hydroxyl group (—OH), or a hydrogen atom, each of $Z_{B1}$, $Z_{B2}$ and $Z_{B3}$ is independently an alkylene group having a carbon number of 1 to 5, an alkenylene group having a carbon number of 2 to 3, *—O—*, *—COO—*, *—OCO—*, *—CF$_2$O—*, *—OCF$_2$—*, a single bond, or a double bond, and each of m1 and m2 is independently 0 or 1.

In an exemplary embodiment, the display device may further include an alignment layer disposed between the insulating substrate and the liquid crystal layer, wherein the alignment layer includes a main alignment layer, which includes a main chain having an imide group as a repeating unit, and an alignment stabilization layer including a cross-linked polymer including a compound having a structure represented by formula C-1:

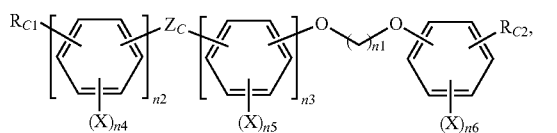

(C-1)

wherein each of $R_{C1}$ and $R_{C2}$ is independently

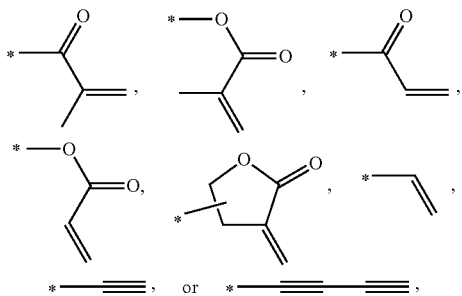

$Z_C$ is an alkylene group, an alkyleneoxy group, an ether group or a single bond, X is a halogen atom, n1 is an integer of 2 to 4, each of n2 and n3 is independently 0 or 1, and each of n4 to n6 is independently an integer of 0 to 2.

In an exemplary embodiment, the liquid crystal layer may further include the compound having the structure represented by formula C-1, wherein the compound having the structure represented by formula C-1 is present in an amount of about 100 ppm or less based on a total weight of the liquid crystal layer.

In an exemplary embodiment, the display device may further include: a first electrode disposed between the insulating substrate and the alignment layer; and a second electrode facing the first electrode, and the liquid crystal layer disposed between the first electrode and the second electrode.

However, aspects of the present disclosure are not restricted to the one set forth herein. The above and other aspects will become more apparent to one of ordinary skill in the art to which the inventive concept pertains by referencing the detailed description provided below.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
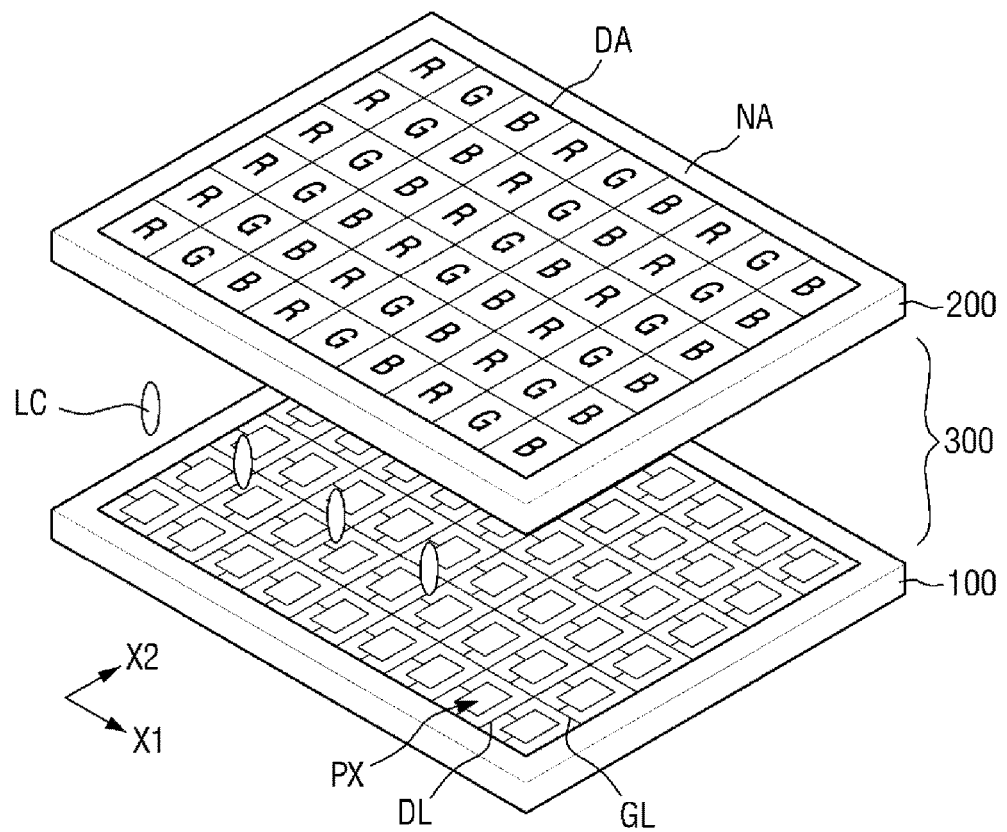
FIG. 1 is an exploded perspective view of a display device according to an exemplary embodiment.

Features of the invention and methods of accomplishing the same may be understood more readily by reference to the following detailed description of various embodiments and the accompanying drawings. The invention may, however, be embodied in many different forms and should not be construed as being limited to the embodiments set forth herein. Rather, these embodiments are provided so that this disclosure will be thorough and complete and will fully convey the concept of the invention to those skilled in the art, and the invention will only be defined by the appended claims.

It will be understood that when an element or layer is referred to as being "on," "connected to" or "coupled to" another element or layer, the element or layer can be directly on, connected or coupled to another element or layer or intervening elements or layers. In contrast, when an element is referred to as being "directly on," "directly connected to" or "directly coupled to" another element or layer, there are no intervening elements or layers present. As used herein, connected may refer to elements being physically, electrically and/or fluidly connected to each other.

Like numbers refer to like elements throughout. As used herein, the term "and/or" includes any and all combinations of one or more of the associated listed items.

It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the invention.

Spatially relative terms, such as "below," "lower," "under," "above," "upper" and the like, may be used herein for ease of description to describe the relationship of one element or feature to another element(s) or feature(s) as illustrated in the figures. It will be understood that the spatially relative terms are intended to encompass different orientations of the device in use or operation, in addition to the orientation depicted in the figures. For example, if the device in the figures is turned over, elements described as "below" or "beneath" relative to other elements or features would then be oriented "above" relative to the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting. As used herein, the singular forms "a," "an" and "the" are intended to include the plural forms as well, including "at least one," unless the context clearly indicates otherwise. It will be further understood that the terms "comprises," "comprising," "includes" and/or "including," when used in this specification, specify the presence of stated features, integers, operations, elements, and/or components, but do not preclude the presence or addition of one or more other features, integers, steps, operations, elements, components, and/or groups thereof. "At least one" is not to be construed as limiting "a" or "an." "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, the symbol "*", as used herein, denotes a bonding site (i.e., a point of attachment) at which adjacent atoms are covalently bonded together.

Unless otherwise defined, the term "alkyl group", as used herein, denotes a monovalent hydrocarbon group where one hydrogen atom is removed from a straight-chain or branched-chain aliphatic saturated hydrocarbon and having the specified number of carbon atoms, and may be represented by "*—$C_nH_{2n+1}$," where n is a natural number. Unless otherwise indicated, alkyl groups include groups having from 1 to 36, or 1 to 24, or 1 to 12 carbon atoms.

Unless otherwise defined, the term "alkoxy group", as used herein, denotes a an alkyl group that is linked via an oxygen atom (i.e., —O-alkyl), and may be represented by "*—O—$C_nH_{2n+1}$," where n is a natural number. Non-limiting examples of C1 to C30 alkoxy groups include methoxy groups, ethoxy groups, propoxy groups, isobutyloxy groups, sec-butyloxy groups, pentyloxy groups, isoamyloxy groups, and hexyloxy groups.

Unless otherwise defined, the term "alkylene group", as used herein, denotes a divalent aliphatic hydrocarbon group where two hydrogen atoms are removed from a straight-chain or branched-chain aliphatic saturated hydrocarbon, which may have from 1 to about 20 carbon atoms, and may be represented by "*—$C_nH_{2n}$—*," where n is a natural number.

Unless otherwise defined, the term "alkenyl" means a straight or branched chain, monovalent hydrocarbon group having at least one carbon-carbon double bond (e.g., ethenyl (*—HC=$CH_2$)). Unless otherwise indicated, alkenyl groups include groups having from 2 to 36, or 2 to 24, or 2 to 12 carbon atoms.

Unless otherwise defined, the term "alkenylene" means a straight or branched chain, divalent hydrocarbon group having at least one carbon-carbon double bond (e.g., ethenylene (*—HC=$CH_2$—*). Unless otherwise indicated, alkenylene groups include groups having from 2 to 36, or 2 to 24, or 2 to 12 carbon atoms.

Unless otherwise defined, the term "alkyleneoxy group", as used herein, denotes a divalent group in which an alkylene group is linked via an oxygen atom, and may be represented by "*—O—$C_nH_{2n}$—*" or "*—$C_nH_{2n}$—O—*," where n is a natural number.

Hereinafter, a liquid crystal composition according to exemplary embodiments will be described.

A liquid crystal composition according to an embodiment includes a compound having a structure represented by formula A-1 below. The compound having the structure represented by formula A-1 may have liquid crystal properties.

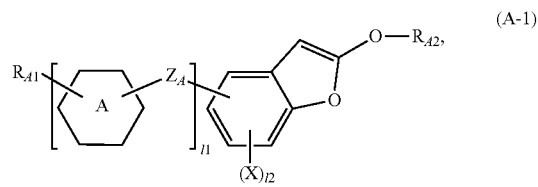

wherein

may be a substituted or unsubstituted aromatic or cycloaliphatic ring structure having a carbon number of 6 or less or a hetero ring structure having a carbon number of 6 or less. For example,

may be

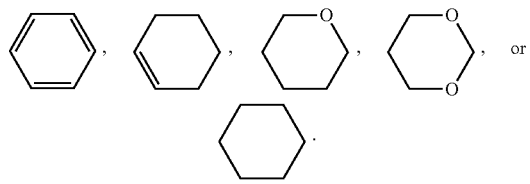

In formula A-1, $Z_A$ may be a connector group. For example, $Z_A$ may be *—O—*, *—COO—*, *—OCO—*, *—$CF_2$O—*, *—$OCF_2$—*, *—$CH_2$O—*, *—$OCH_2$—*, *—$SCH_2$—*, *—$CH_2$S—*, *—$C_2F_4$—*, *—$CH_2CF_2$—*, *—$CF_2CH_2$—*, *—$(CH_2)_k$—* (where k is an integer of 1 to 5), *—CH=CH—*, *—CF=CF—*, *—CH=CF—*, *—CF=CH—*, *—C≡C—*, *—CH=CHCH$_2$O—*, or a single bond.

In formula A-1, l1 may define a repeating unit of

and $Z_A$. For example l1 may be an integer of 0 to 2. In the repeating units defined by l1, i.e., when $l_1$ is 2,

and $Z_A$ may be the same or different. If l1 is within the above range, the compound may have a relatively short length. Accordingly, the compound may have low viscosity properties.

In formula A-1, $R_{A1}$ may be an alkyl group, an alkoxy group, a cyano group, a halogen atom, or a hydrogen atom. For example, $R_{A1}$ may be an alkyl group having a carbon number of 1 to 12, 1 to 10, 1 to 8, 1 to 6, 1 to 5, or 1 to 3, an alkoxy group having a carbon number of 1 to 12, 1 to 10, 1 to 8, 1 to 6, 1 to 5, or 1 to 3, a cyano group, a halogen atom, or a hydrogen atom. The $R_{A1}$ group having a structure as described above, may provide properties such as superior refractive index anisotropy or dielectric anisotropy to the compound. In addition, since the volume of a space occupied by the $R_{A1}$ group is relatively small, the compound may have low viscosity properties.

In formula A-1, $R_{A2}$ may be an alkyl group, a cyano group, a halogen atom, or a hydrogen atom. For example, $R_{A2}$ may be an alkyl group having a carbon number of 1 to 12, 1 to 10, 1 to 8, 1 to 6, 1 to 5, or 1 to 3, a cyano group, a halogen atom, or a hydrogen atom. The $R_{A2}$ group having a structure as described above may provide properties such as superior refractive index anisotropy or dielectric anisotropy to the compound. In addition, since the volume of a space occupied by the $R_{A2}$ group is relatively small, the compound may have low viscosity properties.

In formula A-1, X may be a halogen atom. Examples of the halogen atom may include a fluorine (F) atom, a chlorine (Cl) atom, a bromine (Br) atom, and an iodine (I) atom. In formula A-1, l2 may be an integer of 0 to 2. For example, X may be bonded to a benzofuran group so as to provide high polarity properties to the compound itself.

The compound having the structure represented by formula A-1 includes an oxygen atom bonded directly to the number 2 position of the benzofuran group. In other words, the compound having the structure represented by formula A-1 includes a benzofuran ether structure. An unshared electron pair of the oxygen atom bonded directly to the benzofuran group may have a stereoscopic structure of the benzofuran group and a repulsive force, and as a result, the compound having the structure represented by formula A-1 may have superior dielectric anisotropy, thereby improving transmittance and reducing a driving voltage. Despite its high polarity properties and low viscosity properties, the compound may also have a high phase transition temperature.

Furthermore, the compound having the structure represented by formula A-1 is highly reliable for light, for example, ultraviolet (UV) light having a wavelength band of about 260 to 380 nanometers (nm). Therefore, the liquid crystal composition, when applied to an LCD, may not cause a reduction in the voltage holding ratio or an afterimage defect. This ensures a relatively high refractive index anisotropy and improves the voltage holding ratio properties and the afterimage problem of the liquid crystal display, thereby enhancing display quality.

The compound having the structure represented by formula A-1 may be included in the liquid crystal composition in an amount of about 0.01 to about 20% by weight, based on a total weight of the liquid crystal composition.

In some embodiments, the compound having the structure represented by formula A-1 may be a compound having a structure represented by formula A-2 below:

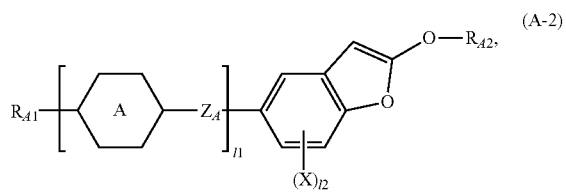

wherein

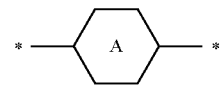

may be

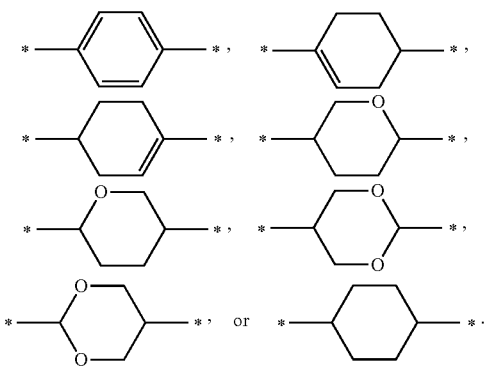

If

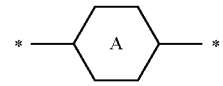

is one of the groups described above, a molecular framework extending from the benzofuran group to the $R_{A1}$ group can be formed in a roughly linear shape. Therefore, it is easy to provide polarity to the compound, and the compound may not interfere with the arrangement of neighboring liquid crystals.

$R_{A1}$ in formula A-2 may be the same as defined in formula A-1. For example, $R_{A1}$ may be an alkyl group having a carbon number of 1 to 5 or 1 to 3, an alkoxy group having a carbon number of 1 to 5 or 1 to 3, a cyano group, a halogen atom, or a hydrogen atom. If $R_{A1}$ is an alkyl group or an alkoxy group, the carbon chain may have a relatively short length, thus further improving the overall viscosity properties of the compound.

In addition, $R_{A2}$ in formula A-2 may be the same as that in formula A-1. For example, $R_{A2}$ may be an alkyl group having a carbon number of 1 to 5 or 1 to 3, a cyano group, a halogen atom, or a hydrogen atom. If $R_{A2}$ is an alkyl group, the carbon chain may have a relatively short length, thus further improving the overall viscosity properties of the compound.

In formula A-2, $Z_A$, X, l1, and l2 are the same as those defined in formula A-1 and thus will not be described in detail.

In some embodiments, the compound having the structure represented by formula A-2 may be a compound having a structure represented by formula A-3, formula A-4, or formula A-4 below:

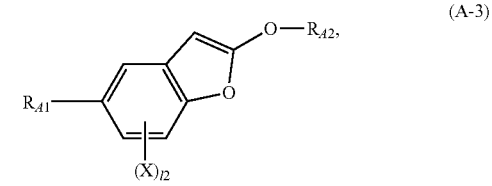
(A-3)

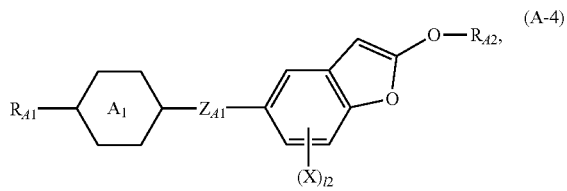
(A-4)

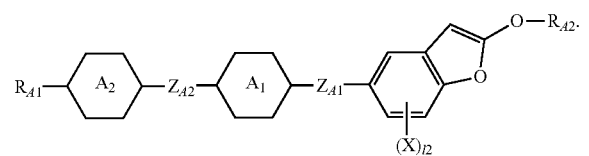
(A-5)

In formulas A-4 and A-5,

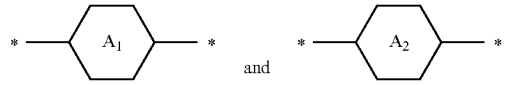

may be independently selected from the same substituents as

For example,

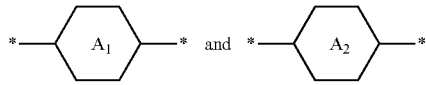

and may be independently,

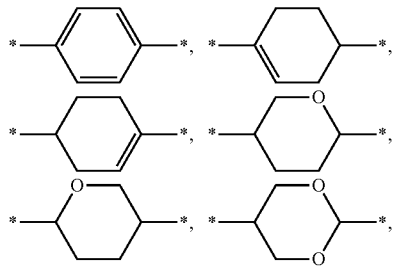

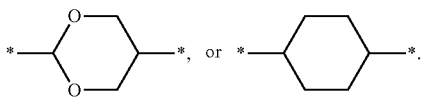

In formulas A-4 and A-5, $Z_{A1}$ and $Z_{A2}$ may be independently selected from the same substituents as $Z_A$. For example, $Z_A$ may be *—O—*, *—COO—*, *—OCO—*, *—CF$_2$O—*, *—OCF$_2$—*, *—CH$_2$O—*, *—OCH$_2$—*, *—SCH$_2$—*, *—CH$_2$S—*, *—C$_2$F$_4$—*, *—CH$_2$CF$_2$—*, *—CF$_2$CH$_2$—*, *—(CH$_2$)$_k$—* (where k is an integer of 1 to 5), *—CH=CH—*, *—CF=CF—*, *—CH=CF—*, *—CF=CH—*, *—C≡C—*, *—CH=CHCH$_2$O—*, or a single bond.

$R_{A1}$, $R_{A2}$, X, and l2 in formulas A-3 through A-5 are the same as those defined in formula A-2 and thus will not be described in detail.

In some embodiments, the compound having the structure represented by formula A-3, formula A-4, or formula A-5 may be a compound having a structure represented by any one of formulas A-6 through A-13 below:

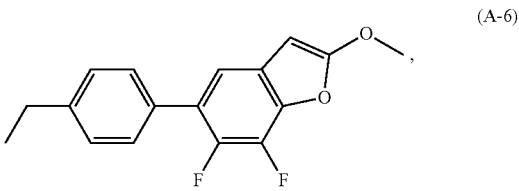
(A-6)

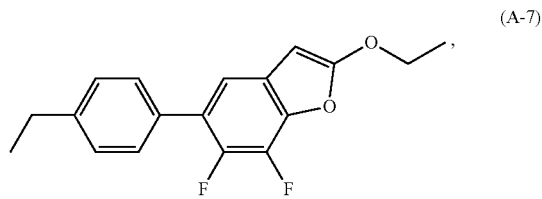
(A-7)

(A-8)

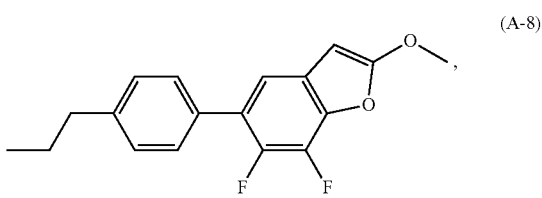
(A-9)

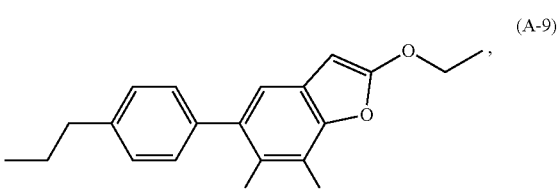
(A-10)

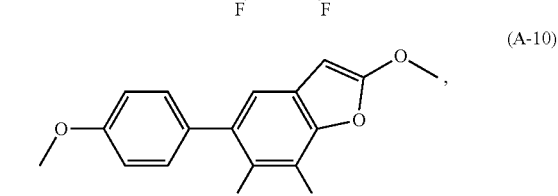

(A-11)

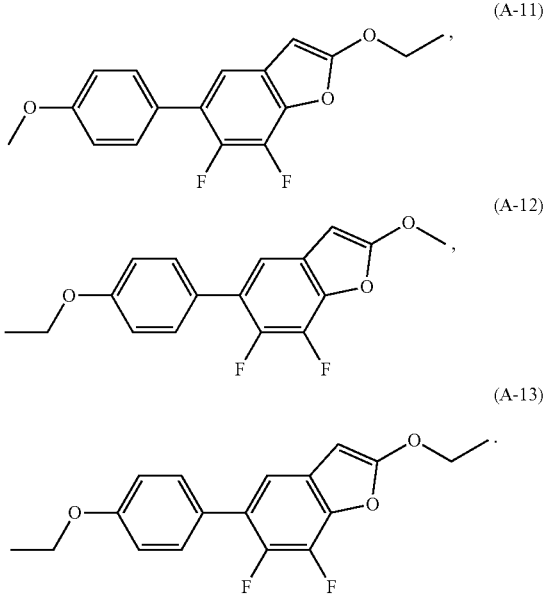

(A-12)

(A-13)

The compound having the structure represented by any one of formulas A-6 through A-13 may have a refractive index anisotropy (Δn) of about 0.230 to about 0.260 and a rotational viscosity at 20° C. (γ 1, 20° C.) of about 70 to about 100 millipascal-seconds (mPas).

In an exemplary embodiment, the liquid crystal composition may include one or more of the compounds having the structures represented by formulas A-6 through A-13. In some embodiments, the liquid crystal composition may include two or more of the compounds having the structures represented by formulas A-6 through A-13.

In an exemplary embodiment, the liquid crystal composition may further include a compound having a structure represented by formula B-1 below. The compound having the structure represented by formula B-1 may be a stabilizer compound:

(B-1)

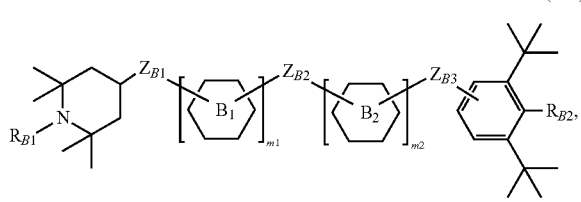

wherein each of

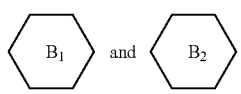

and may be independently a substituted or unsubstituted aromatic or cycloaphatic ring structure having a carbon number of 6 or less or a hetero ring structure having a carbon number of 6 or less. For example, each of

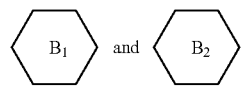

may be independently

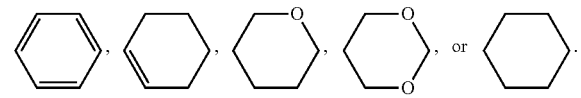

In formula B-1, each of m1 and m2 may define a molecular framework structure positioned between a cycloamine group and a benzene group. For example, each of m1 and m2 may be independently 0 or 1.

In formula B-1, each of $Z_{B1}$, $Z_{B2}$, and $Z_{B3}$ may be a connector group. For example, each of $Z_{B1}$, $Z_{B2}$ and $Z_{B3}$ may be independently an alkylene group having a carbon number of 1 to 5, an alkenylene group having a carbon number of 2 to 3, *—O—*, *—COO—*, *—OCO—*, *—CF$_2$O—*, *—OCF$_2$—*, a single bond, or a double bond.

In formula B-1, $R_{B1}$ may be an alkyl group, an alkoxy group, or a hydrogen atom. For example, $R_{B1}$ may be an alkyl group having a carbon number of 1 to 12, 1 to 10, 1 to 8, 1 to 6, 1 to 5, or 1 to 3, an alkoxy group having a carbon number of 1 to 12, 1 to 10, 1 to 8, 1 to 6, 1 to 5, or 1 to 3, or a hydrogen atom. If $R_{B1}$ is one of the structures as described above, the group can effectively suppress the unintended reaction of liquid crystals.

$R_{B2}$ may be an alkyl group, an alkoxy group, an acetamide group (—NHCOCH$_3$), a hydroxyl group (—OH), or a hydrogen atom. For example, $R_{B2}$ may be an alkyl group having a carbon number of 1 to 12, 1 to 10, 1 to 8, 1 to 6, 1 to 5, or 1 to 4, an alkoxy group having a carbon number of 1 to 12, 1 to 10, 1 to 8, 1 to 6, 1 to 5, or 1 to 4, an acetamide group, a hydroxyl group, or a hydrogen atom. If $R_{B2}$ is one of the structures as described above, the group can effectively suppress the unintended reaction of liquid crystals.

The compound having the structure represented by formula B-1 includes a cycloamine group and abenzene group at each end of the compound. Therefore, the compound is capable of preventing oxidation and suppressing the mechanism by which ion impurities are formed by light or heat, thereby increasing the reliability of the liquid crystal composition. If the liquid crystal composition according to the current embodiment is applied to an LCD, it can improve the voltage holding ratio and effectively prevent the formation of an afterimage, which occurs due to the presence of impurities.

The compound having the structure represented by formula B-1 may be included in the liquid composition in an amount of about 50 to about 3,000 parts per million (ppm), based on the total weight of the liquid crystal composition.

In some embodiments, the compound having the structure represented by formula B-1 may be a compound having a structure represented by formula B-2 below:

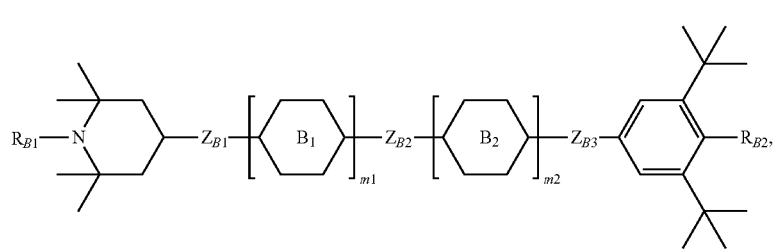
(B-2)

wherein each of

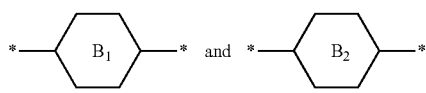

and may be independently,

*—⬡—*, *—⬡—*,
*—⬡—*, *—⬡(O)—*,
*—(O)⬡(O)—*, *—(O)⬡(O)—*,
*—(O,O)⬡—*, or *—⬡—*.

If

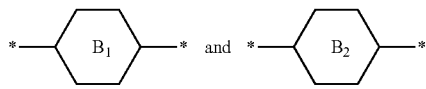

and have a structure as described above, a molecular framework extending from the cycloamine group to the benzene group can be formed in a roughly linear shape. This is advantageous in providing low viscosity properties to the liquid crystal composition, and the compound may not interfere with the arrangement of liquid crystals in the liquid crystal layer.

$R_{B1}$ in formula B-2 may be the same as defined in formula B-1. For example, $R_{B1}$ may be an alkyl group having a carbon number of 1 to 5 or 1 to 3, an alkoxy group having a carbon number of 1 to 5 or 1 to 3, or a hydrogen atom.

In addition, $R_{B2}$ in formula B-2 may be the same as defined in formula B-1. For example, $R_{B2}$ may be an alkyl group having a carbon number of 1 to 5 or 1 to 4, an alkoxy group having a carbon number of 1 to 5 or 1 to 4, an acetamide group, a hydroxyl group, or a hydrogen atom.

$Z_{B1}$, $Z_{B2}$, $Z_{B3}$, m1, and m2 in formula B-2 are the same as those defined in formula B-1 and thus will not be described in detail.

In some embodiments, the compound having the structure represented by formula B-2 may be a compound having a structure represented by formula B-3, formula B-4, or formula B-5 below:

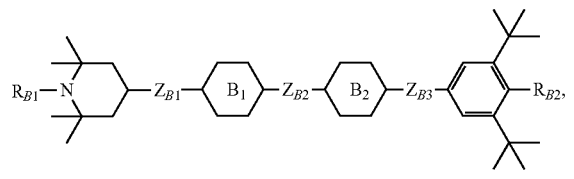
(B-3)

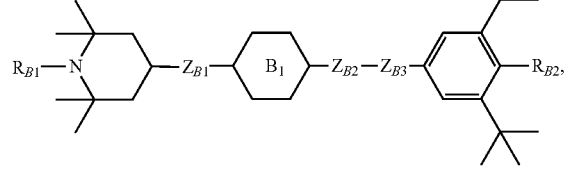
(B-4)

(B-5)

Where

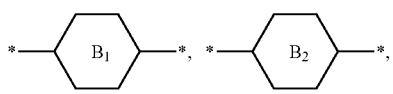

$R_{B1}$, $R_{B2}$, $Z_{B1}$, $Z_{B2}$ and $Z_{B3}$ in formulas B-3 through B-5 are the same as those in formula B-2 and thus will not be described in detail.

In some embodiments, each of the compounds having the structures represented by formulas B-3 through B-5 may be a compound having a structure represented by any one of formulas B-6 through B-9 below:

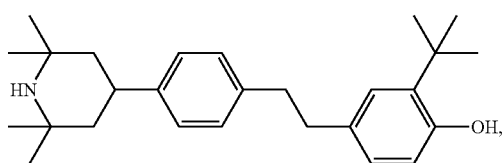
(B-6)

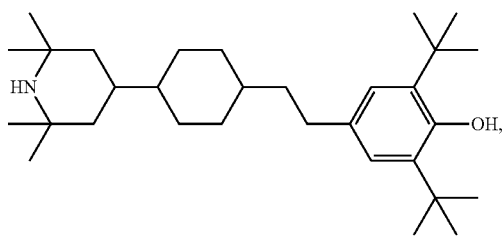
(B-7)

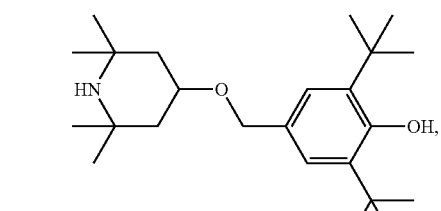
(B-8)

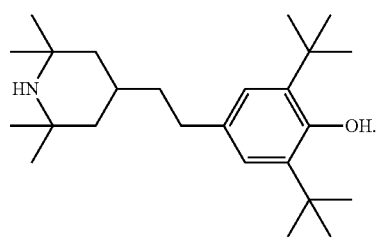
(B-9)

In an exemplary embodiment, the liquid crystal composition may further include a compound having a structure represented by formula C-1 below. The compound having the structure represented by formula C-1 may be a polymeric compound:

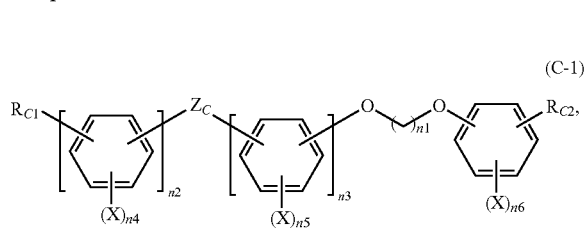
(C-1)

wherein $Z_C$ may be a connector group. In an example, $Z_C$ may be an alkylene group, an alkyleneoxy group, an ether group, or a single bond. In another example, $Z_C$ may be an alkylene group having a carbon number of 1 to 3, an alkyleneoxy group having a carbon number of 1 to 3, an ether group, or a single bond.

In formula C-1, n1 may be an integer of 2 to 4. In addition, in formula C-1, each of n2 and n3 may define a molecular framework structure. For example, each of n2 and n3 may be independently 0 or 1.

In formula C-1, X may be a halogen atom. Examples of the halogen atom may include a fluorine atom, a chlorine atom, a bromine atom, and an iodine atom. In formula C-1, each of n4 through n6 may be independently an integer of 0 to 2. For example, X may be bonded to a benzene group so as to provide high polarity properties to the compound.

In formula C-1, each of $R_{C1}$ and $R_{C2}$ may be a polymerizable reactive group to facilitate polymerization. For example, each of $R_{C1}$ and $R_{C2}$ may be independently

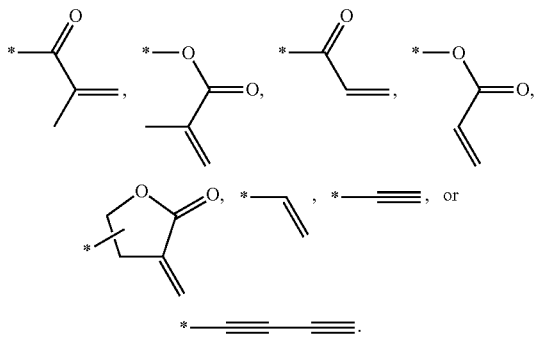

The compound having the structure represented by formula C-1 may be polymerized to form a polymer. The polymerization reaction may be initiated by exposure to light or heat. For example, the compound having the structure represented by formula C-1 may be polymerized as it absorbs light having a wavelength band of about 260 to about 380 nm or about 350 to about 380 nm.

The compound having the structure represented by formula C-1 may be included in an amount of greater than about 100 to about 1,000 ppm or about 1,000 to about 10,000 ppm, based on the total weight of the liquid crystal composition.

In some embodiments, the compound having the structure represented by formula C-1 may be a compound having a structure represented by formula C-2 below:

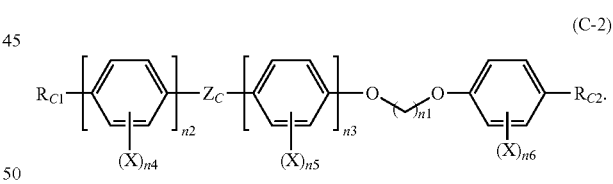
(C-2)

$R_{C1}$, $R_{C2}$, $Z_C$, X and n1 through n6 in formula C-2 are the same as those defined in formula C-1 and thus will not be described in detail.

In some embodiments, the compound having the structure represented by formula C-2 may be a compound having a structure represented by formula C-3 or C-4 below:

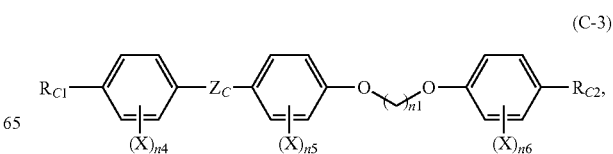
(C-3)

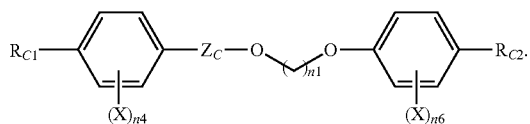

(C-4)

In formulas C-3 and C-4, $R_{C1}$, $R_{C2}$, $Z_C$, X, n1, n4, and n6 are the same as those defined in formula C-1 and thus will not be described in detail.

In some embodiments, the compound having the structure represented by formula C-3 or C-4 may be a compound having a structure represented by any one of formulas C-5 and through C-8 below:

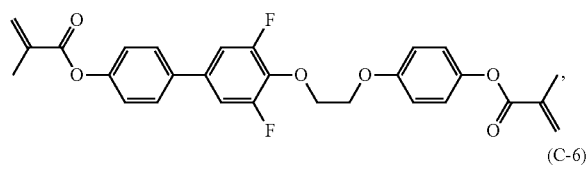

(C-5)

(C-6)

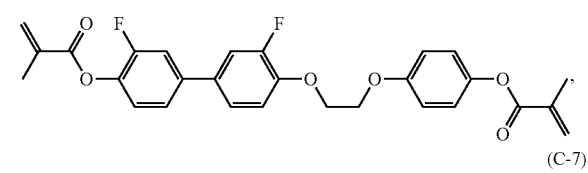

(C-7)

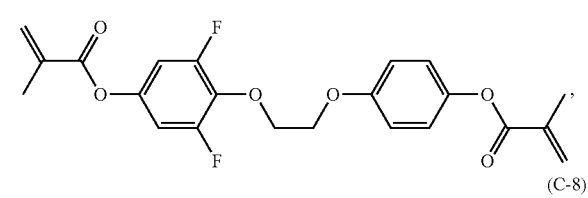

(C-8)

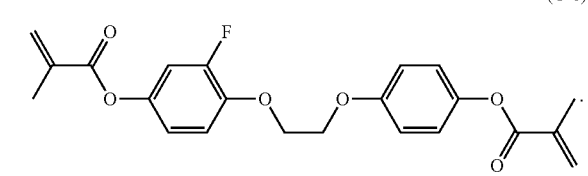

In an exemplary embodiment, the liquid crystal composition may further include a polymerization initiator such as a photopolymerization initiator or a thermal polymerization initiator.

The liquid crystal composition may have a refractive index anisotropy (Δn) of about 0.080 to about 0.120, a dielectric anisotropy (Δε) of about −5.5 to about −2.8, and a rotational viscosity at 20° C. ($\gamma$ 1, 20° C.) of about 70 to about 110 mPas. Therefore, if the liquid crystal composition is applied to an LCD, the liquid crystal composition can ensure high light transmittance, improve the voltage holding ratio, and suppress the formation of an afterimage, thereby enhancing display quality.

Hereinafter, a display device according to various embodiments of the inventive concept will be described with reference to the attached drawings.

FIG. 1 is an exploded perspective view of a display device according to an exemplary embodiment.

Referring to FIG. 1, the display device according to the current embodiment includes a first display substrate 100, a second display substrate 200, which faces the first display substrate 100, and a liquid crystal layer 300, which is disposed between the first display substrate 100 and the second display substrate 200. The liquid crystal layer 300 may include a plurality of liquid crystals LC, and the liquid crystal layer 300 and the liquid crystals LC may have negative dielectric anisotropy.

The display device includes a display area DA and a non-display area NA. The display area DA may be an area in which an image is displayed, and the non-display area NA may be a light-blocking area which surrounds the display area DA. The display area DA includes a plurality of pixels PX. Each of the pixels PX may uniquely display one of the primary colors. For example, the pixels PX may include a red pixel R, which displays a red color, a green pixel G, which displays a green color, and a blue pixel B, which displays a blue color. The red pixel R, the green pixel G, and the blue pixel B may be repeatedly arranged along a first direction X1 and a second direction X2 to form a matrix shape when observed from a position above the display device. A plurality of gate lines GL and a plurality of data lines DL may respectively extend along the first direction X1 and the second direction X2 and may respectively deliver gate driving signals and data driving signals to the pixels PX.

Figure 2:
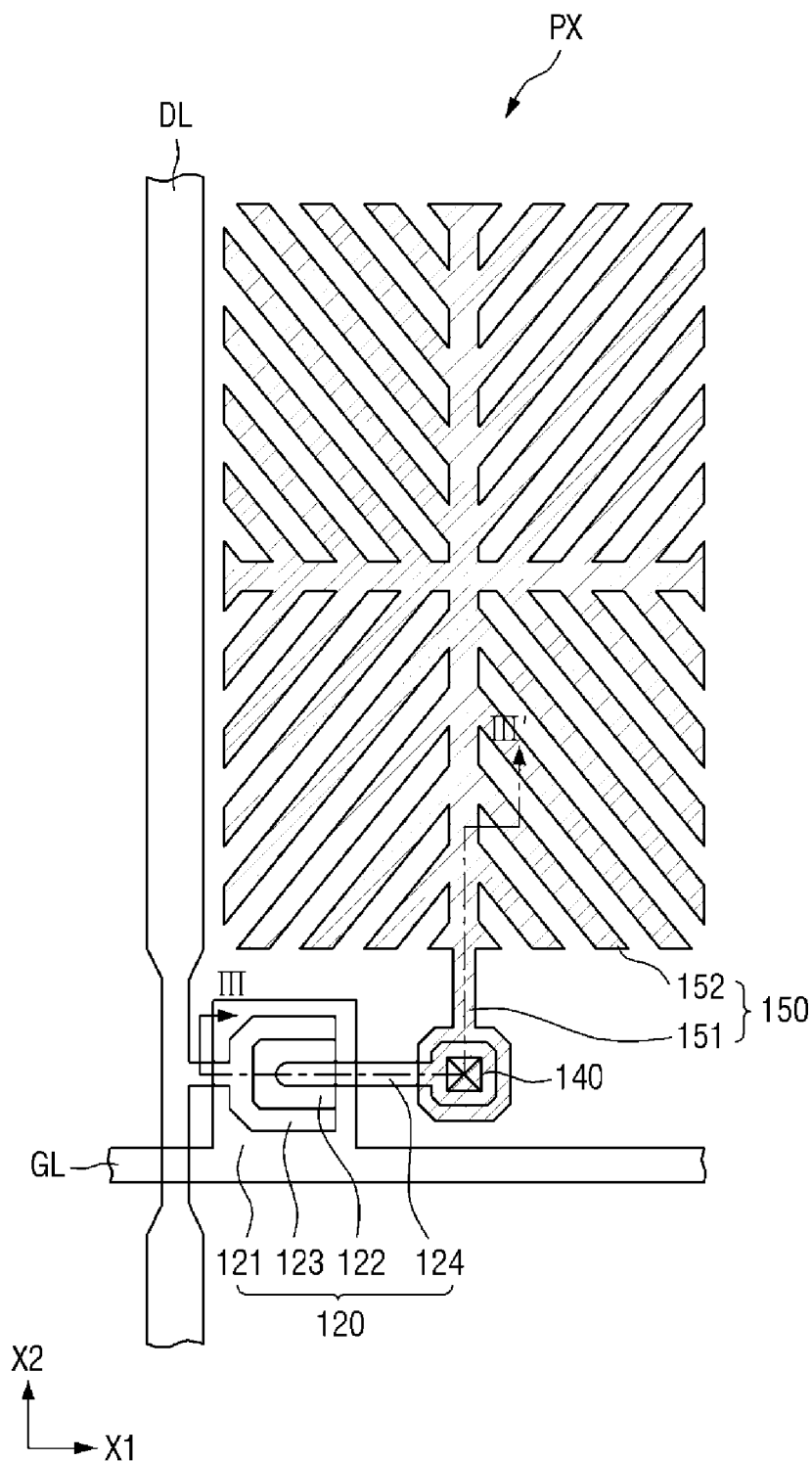
FIG. 2 is a plan view of a pixel of a first display substrate included in the display device of FIG. 1.
Figure 3:
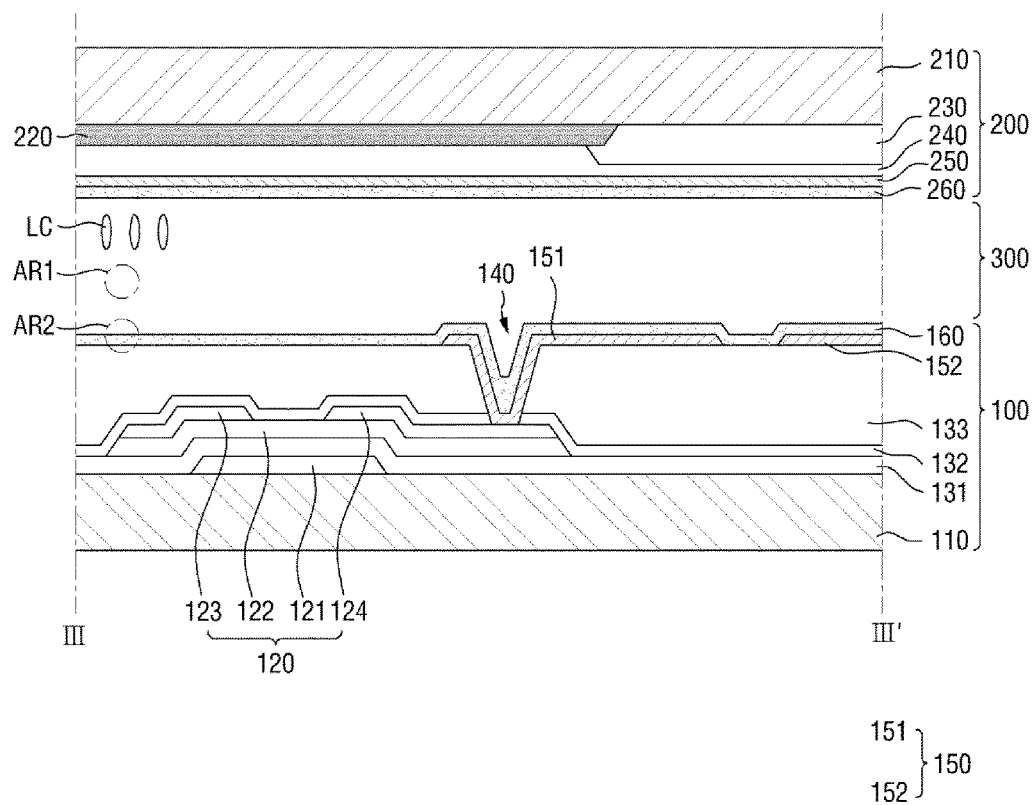
FIG. 3 is a cross-sectional view taken along the line III-III' of the display device including the first display substrate of FIG. 2.
Figure 4:
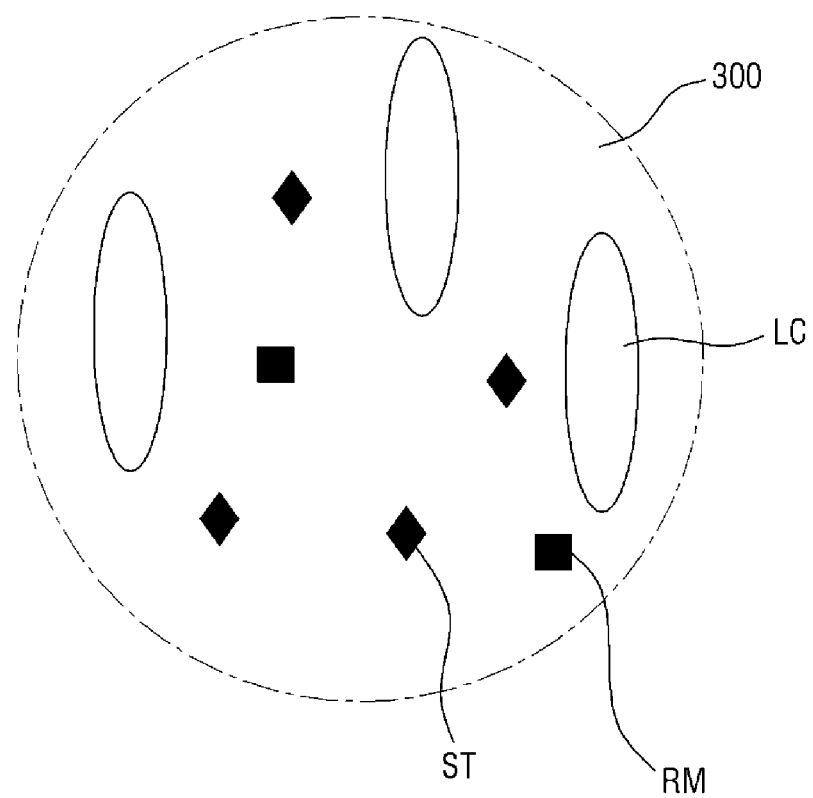
FIG. 4 is an enlarged cross-sectional view of an area "AR1'" of FIG. 3.
Figure 5:
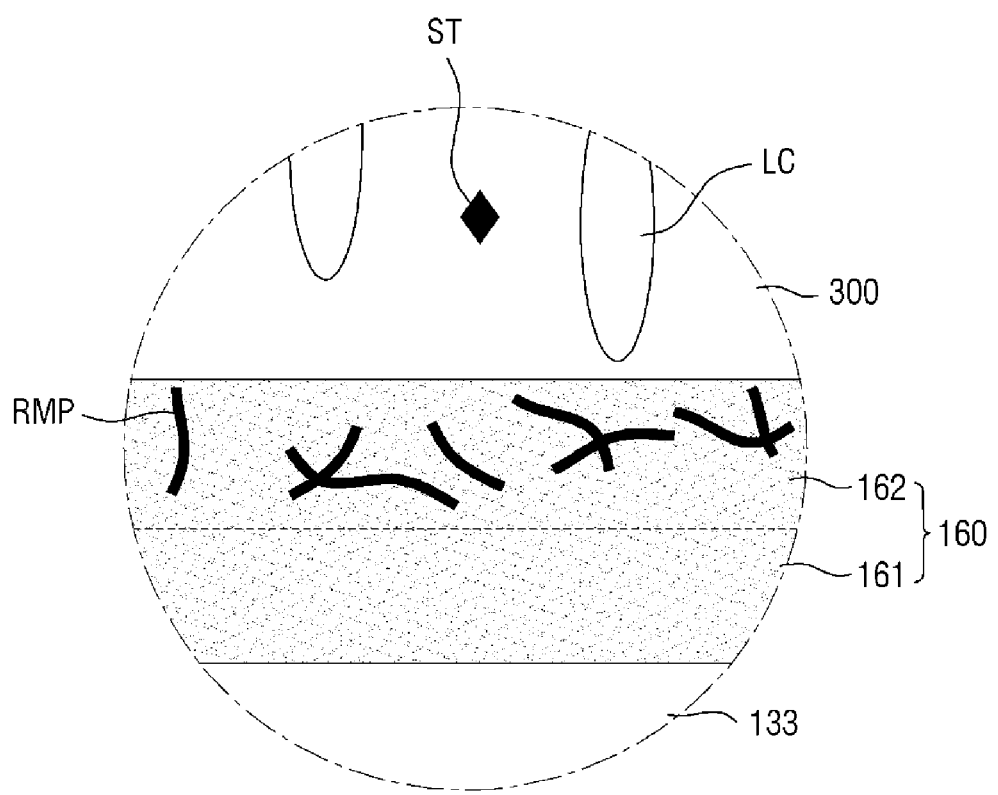
FIG. 5 is an enlarged cross-sectional view of an area "AR2" of FIG. 3.

FIG. 2 is a plan view of a pixel PX of the first display substrate 100 included in the display device of FIG. 1. FIG. 3 is a cross-sectional view taken along the line III-III' of the display device including the first display substrate 100 of FIG. 2. FIG. 4 is an enlarged cross-sectional view of the area labelled AR1 in FIG. 3. FIG. 5 is an enlarged cross-sectional view of the area labelled AR2 in FIG. 3.

Referring to FIGS. 1 through 5, a switching device 120 for controlling the alignment direction of the liquid crystals LC in the liquid crystal layer 300 is disposed on the first display substrate 100, and the second display substrate 200 may be a counter substrate which is separated from the first display substrate 100 with the liquid crystal layer 300 interposed between the first substrate and the second substrate.

In an exemplary embodiment, the first display substrate 100 includes a first insulating substrate 110, the switching device 120 disposed on the first insulating substrate 110, and a first electrode 150 disposed on the switching device 120.

The first insulating substrate 110 may be a transparent insulating substrate. For example, the first insulating substrate 110 may be a glass or plastic substrate. In some embodiments, the first insulating substrate 110 may have flexibility.

The switching device 120 is disposed on the first insulating substrate 110. The switching device 120 may be a thin-film transistor (TFT) including a gate electrode 121 disposed on the first insulating substrate 110, an active layer 122 disposed on the gate electrode 121, and a source electrode 123 and a drain electrode 124 disposed on the active layer 122 in a manner so as to be separated from each other.

The gate electrode 121 which is a control terminal may be connected to a gate line GL to receive a gate driving signal, the source electrode 123 which is an input terminal may be connected to a data line DL to receive a data driving signal, and the drain electrode 124 which is an output terminal may be electrically connected to the first electrode 150 by a contact hole 140. The active layer 122 may serve as a channel of the TFT and may turn the channel on or off according to a voltage applied to the gate electrode 121.

The gate electrode 121 and the active layer 122 may be electrically insulated from one another by an insulating layer 131 disposed between the gate electrode 121 and the active layer 12. A passivation layer 132 may be disposed on the active layer 122, the source electrode 123, and the drain electrode 124, and may prevent electrodes disposed under the passivation layer 132 from directly contacting an organic material. The insulating layer 131 and the passivation layer 132 may be made of an inorganic material. Examples of the inorganic material may include silicon nitride (SiNx), silicon oxide (SiOx), silicon nitride oxide (SiNxOy), and silicon oxynitride (SiOxNy). An organic layer 133 may be disposed on the passivation layer 132. The organic layer 133 may be a planarization layer which planarizes a plurality of elements stacked on the first insulating substrate 110 to have uniform heights. In an embodiment, the organic layer 133 may be omitted.

The first electrode 150 may be disposed on the organic layer 133. The first electrode 150 may be a pixel electrode which is disposed in each pixel PX and controlled by a data driving signal. In FIG. 3, the first electrode 150 is disposed on the first display substrate 100, and a second electrode 250 is disposed on the second display substrate 200. In an embodiment, the first electrode 150 and the second electrode 250 may also be disposed on the same substrate.

The first electrode 150 may be a transparent electrode. The transparent electrode may be made of a material such as indium tin oxide (ITO) or indium zinc oxide (IZO). The first electrode 150 may include a plurality of micro-branch electrodes 152, and a micro-slit may be formed between each pair of adjacent micro-branch electrodes 152. For example, the first electrode 150 may include a stem electrode which is shaped roughly like a cross (+), a plurality of micro-branch electrodes 152 which extend radially from the stem electrode in a direction about 45 degrees relative to the stem electrode, and a connecting electrode 151 which protrudes from the stem electrode toward the contact hole 140 and is connected to the drain electrode 124. The first electrode 150 may form an electric field in the liquid crystal layer 300 together with the second electrode 250, thereby controlling the alignment direction of the liquid crystals LC.

A first alignment layer 160 may be disposed on the first electrode 150. The first alignment layer 160 may include a first main alignment layer 161 and a first alignment stabilization layer 162.

The first main alignment layer 161 may be disposed on the first electrode 150. The first main alignment layer 161 may be a copolymer of a dianhydride compound and a diamine compound. The first main alignment layer 161 may include a polymer chain which includes polyamic acid having an imide group (—CONRCO—) as a repeating unit of a main chain, a polymer obtained by partial imidization of polyamic acid having an imide group as a repeating unit, polyimide obtained by dehydrative cyclization of polyamic acid having an imide group as a repeating unit, or a combination thereof.

The polymer chain of the first main alignment layer 161 may include side chains attached to the polymer chain. At least some of side chains attached to the polymer chain of the first main alignment layer 161 may include a vertical alignment group. The vertical alignment group may induce the initial vertical alignment of the liquid crystals LC in the liquid crystal layer 300. The vertical alignment group may be cured such that is has a specific slope relative to an alignment surface.

In some embodiments, at least some of the side chains of the polymer chain may further include a polymerization initiator and/or an ion scavenger.

The first alignment stabilization layer 162 may be disposed on the first main alignment layer 161. The first alignment stabilization layer 162 may be disposed between the first main alignment layer 161 and the liquid crystal layer 300. For example, the first alignment stabilization layer 162 may be formed in the shape of micro-protrusions and may cover an entire surface of the first main alignment layer 161. The first alignment stabilization layer 162 may enable the side chains (e.g., the vertical alignment groups) of the polymer chain in the first main alignment layer 161 to maintain a predetermined slope and may improve the hardness of the first alignment layer 160. The first alignment stabilization layer 162 may include a polymer compound RMP obtained by polymerization of monomeric and/or polymeric compounds or by polymerization and chemical bonding between a polymeric compound and the side chains (e.g., the vertical alignment groups) of the polymer chain in the first main alignment layer 161.

In an exemplary embodiment, the first alignment stabilization layer 162 may include a crosslinked polymer of a compound having a structure represented by formula C-1 below:

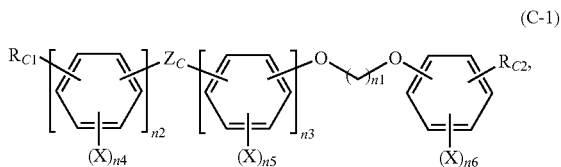

(C-1)

wherein $Z_C$ may be a connector group. In an example, $Z_C$ may be an alkylene group, an alkyleneoxy group, an ether group, or a single bond. In another example, $Z_C$ may be an alkylene group having a carbon number of 1 to 3, an alkyleneoxy group having a carbon number of 1 to 3, an ether group, or a single bond.

In formula C-1, n1 may be an integer of 2 to 4. In addition, in formula C-1, each of n2 and n3 may define a molecular framework structure. For example, each of n2 and n3 may be independently 0 or 1.

In formula C-1, X may be a halogen atom. Examples of the halogen atom may include a fluorine atom, a chlorine atom, a bromine atom, and an iodine atom. In formula C-1, each of n4 through n6 may be independently an integer of 0 to 2.

In formula C-1, each of $R_{C1}$ and $R_{C2}$ may be a polymerizable reactive group used to facilitate polymerization. For example, each of $R_{C1}$ and $R_{C2}$ may be independently

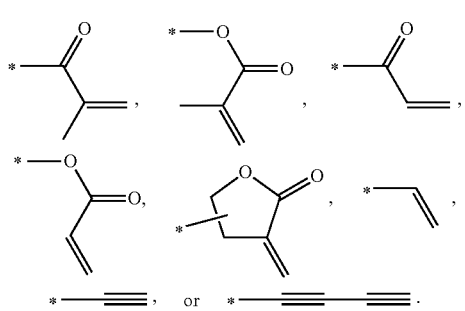

In some embodiments, the compound having the structure represented by formula C-1 may be any one of the compounds having the structures represented by formulas C-2 through C-8 described above. Since the compounds having the structures represented by formulas C-2 through C-8 have been previously described together with the liquid crystal composition according to the embodiment, a detailed description of the compounds will be omitted.

The second display substrate 200 includes a second insulating substrate 210, a light-blocking member 220 and a color filter 230 disposed on the second insulating substrate 210, and the second electrode 250 disposed on the light-blocking member 220 and the color filter 230.

Similar to the first insulating substrate 110, the second insulating substrate 210 may be a transparent insulating substrate. The light-blocking member 220 may be made of a material that blocks transmission of light by absorbing or reflecting light of at least a particular wavelength band. For example, the light-blocking member 220 may be a black matrix. The light-blocking member 220 may be disposed at a boundary between adjacent pixels PX to prevent color mixing and a color mixture defect. The color filter 230 may be made of a material that absorbs a particular wavelength band of incident light or that shifts or converts a wavelength of incident light to a particular wavelength. That is, the color filter 230 may transmit light of a particular wavelength band only. In FIG. 3, the light-blocking member 220 and the color filter 230 are disposed on the second display substrate 200. However, one or more of the light-blocking member 220 and the color filter 230 can also be disposed on the first display substrate 100. An overcoat layer 240 may be disposed on the light-blocking member 220 and the color filter 230. The overcoat layer 240 may be made of an organic material. The overcoat layer 240 may provide a uniform height to a plurality of elements stacked on the second insulating substrate 210.

The second electrode 250 may be disposed on the overcoat layer 240. The second electrode 250 may be a common electrode disposed in the pixels PX and to which a common voltage is applied. The second electrode 250 may form a vertical electric field in the liquid crystal layer 300 together with the first electrode 150.

A second alignment layer 260 may be disposed on the second electrode 250. The second alignment layer 260 may include a second main alignment layer and a second alignment stabilization layer. The second main alignment layer may be disposed on the second electrode 250 and between the second main alignment layer and the liquid crystal layer 300. The second main alignment layer may include a polymer chain having an imide group as a repeating unit. The second alignment stabilization layer may include one of the compounds having the structures represented by formulas C-1 through C-8 described above. The second alignment layer 260 may be the same as the first alignment layer 160 except for the position of the second alignment layer 260, and thus will not be described in detail.

The liquid crystal layer 300 includes a plurality of liquid crystals LC. In an exemplary embodiment, the liquid crystals LC and a liquid crystal composition that forms the liquid crystal layer 300 may have negative dielectric anisotropy. In an initial alignment state, the liquid crystals LC may remain in a stable position because long axes of the liquid crystals LC are aligned roughly perpendicular to the alignment surface. In some embodiments, the liquid crystals LC may be stably maintained with a specific pretilt angle. The pretilt angle may be stabilized by the sloping side chains (e.g., the vertical alignment groups) of the polymer chain in the first and second main alignment layers and by the polymer compound RMP in the first and second alignment stabilization layers. The liquid crystals LC having negative dielectric anisotropy may be tilted by a vertical electric field formed by the first electrode 150 and the second electrode 250, such that the long axes of the liquid crystals LC form a specific predetermined angle relative to the direction of the electric field. As the direction of the long axes of the liquid crystals LC changes, the amount of light that transmits through the liquid crystal layer 300 may be adjusted. The term "initial alignment state," as used herein, denotes the alignment state of the liquid crystals LC when no electric field has been formed in the liquid crystal layer 300.

In an exemplary embodiment, the liquid crystals LC of the liquid crystal layer 300 include a compound having a structure represented by formula A-1 below:

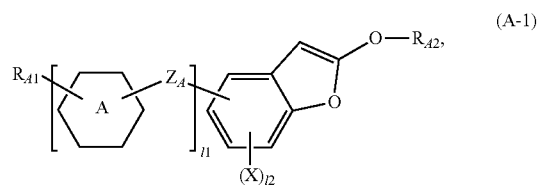

wherein

may be a substituted or unsubstituted aromatic or cycloaliphatic ring structure having a carbon number of 6 or less or a hetero ring structure having a carbon number of 6 or less. For example,

may be

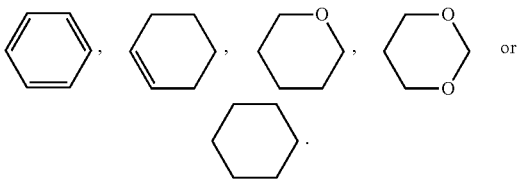

In formula A-1, $Z_A$ may be a connector group. For example, $Z_A$ may be *—O—*, *—COO—*, *—OCO—*, *—CF$_2$O—*, *—OCF$_2$—*, *—CH$_2$O—*, *—OCH$_2$—*, *—SCH$_2$—*, *—CH$_2$S—*, *—C$_2$F$_4$—*, *—CH$_2$CF$_2$—*, *—CF$_2$CH$_2$—*, *—(CH$_2$)$_k$—* (where k is an integer of 1 to 5), *—CH=CH—*, *—CF=CF—*, *—CH=CF—*, *—CF=CH—*, *—C≡C—*, *—CH=CHCH$_2$O—*, or a single bond.

In formula A-1, l1 may define a repeating unit of

and $Z_4$. For example, l1 may be an integer of 0 to 2. If l1 is 2,

and $Z_4$ in a repeating unit defined by l1, may be the same or may be different.

In formula A-1, $R_{A1}$ may be an alkyl group, an alkoxy group, a cyano group, a halogen atom, or a hydrogen atom. For example, $R_{A1}$ may be an alkyl group having a carbon number of 1 to 12, 1 to 10, 1 to 8, 1 to 6, 1 to 5, or 1 to 3, an alkoxy group having a carbon number of 1 to 12, 1 to 10, 1 to 8, 1 to 6, 1 to 5, or 1 to 3, a cyano group, a halogen atom, or a hydrogen atom.

In formula A-1, $R_{A2}$ may be an alkyl group, a cyano group, a halogen atom, or a hydrogen atom. For example, $R_{A2}$ may be an alkyl group having a carbon number of 1 to 12, 1 to 10, 1 to 8, 1 to 6, 1 to 5, or 1 to 3, a cyano group, a halogen atom, or a hydrogen atom.

In formula A-1, X may be a halogen atom. Examples of the halogen atom may include a fluorine atom, a chlorine atom, a bromine atom, and an iodine atom. In formula A-1, l2 may be an integer of 0 to 2. For example, X may be bonded to a benzofuran group so as to provide high polarity properties to the compound.

The compound having the structure represented by formula A-1 may have superior dielectric anisotropy, thereby improving transmittance and reducing a driving voltage. Despite its high polarity properties and low viscosity properties, the compound may also have a high phase transition temperature. Furthermore, the compound having the structure represented by formula A-1 is highly reliable for light, for example, UV light having a wavelength band of about 260 to about 380 nm. Therefore, the compound, when applied to an LCD, may not cause a reduction in the voltage holding ratio or an afterimage defect. This ensures a relatively high refractive index anisotropy and improves the voltage holding ratio properties and the afterimage problem, thereby enhancing display quality.

In some embodiments, the compound having the structure represented by formula A-1 may be any one of the compounds having the structures represented by formulas A-2 through A-13 described above. Since the compounds having the structures represented by formulas A-2 through A-13 have been previously described together with the liquid crystal composition according to the embodiment, a detailed description of the compounds will be omitted.

In an exemplary embodiment, the liquid crystal layer 300 may further include a compound ST (see FIGS. 4 and 5) having a structure represented by formula B-1 below:

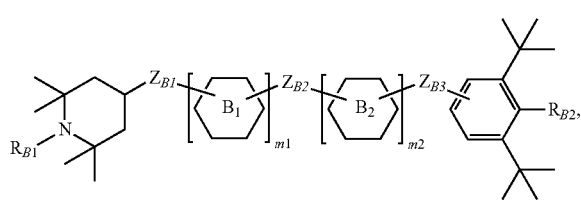

(B-1)

wherein each of

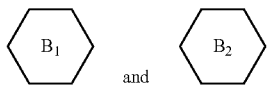

may be independently a substituted or unsubstituted aromatic or cycloalphatic ring structure having a carbon number of 6 or less, or a hetero ring structure having a carbon number of 6 or less. For example, each of

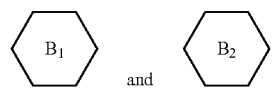

may be independently

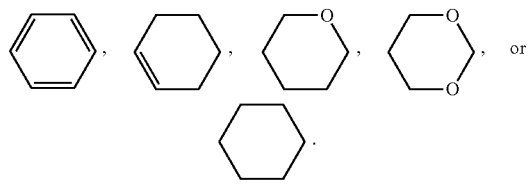

In formula B-1, each of m1 and m2 may define a molecular framework structure between the cycloamine group and the benzene group. For example, each of m1 and m2 may be independently 0 or 1.

In formula B-1, each of $Z_{B1}$, $Z_{B2}$, and $Z_{B3}$ may be a connector group. For example, each of $Z_{B1}$, $Z_{B2}$ and $Z_{B3}$ may be independently an alkylene group having a carbon number of 1 to 5, an alkenylene group having a carbon number of 2 to 3, *—O—*, *—COO—*, *—OCO—*, *—CF$_2$O—*, *—OCF$_2$—*, a single bond, or a double bond.

In formula B-1, $R_{B1}$ may be an alkyl group, an alkoxy group, or a hydrogen atom. For example, $R_{B1}$ may be an alkyl group having a carbon number of 1 to 12, 1 to 10, 1 to 8, 1 to 6, 1 to 5, or 1 to 3, an alkoxy group having a carbon number of 1 to 12, 1 to 10, 1 to 8, 1 to 6, 1 to 5, or 1 to 3, or a hydrogen atom.

$R_{B2}$ may be an alkyl group, an alkoxy group, an acetamide group (—NHCOCH$_3$), a hydroxyl group (—OH), or a hydrogen atom. For example, $R_{B2}$ may be an alkyl group having a carbon number of 1 to 12, 1 to 10, 1 to 8, 1 to 6, 1 to 5, or 1 to 4, an alkoxy group having a carbon number of 1 to 12, 1 to 10, 1 to 8, 1 to 6, 1 to 5, or 1 to 4, an acetamide group, a hydroxyl group, or a hydrogen atom.

The compound ST having the structure represented by formula B-1 includes a cycloamine group and a benzene group. Therefore, the compound ST can prevent oxidation and suppress the mechanism by which ion impurities are formed in response to light or heat, thereby improving the voltage holding ratio and effectively preventing the afterimage problem due to impurities.

In some embodiments, the compound ST having the structure represented by formula B-1 may be any one of the compounds having the structures represented by formulas B-2 through B-9 described above. Since the compounds having the structures represented by formulas B-2 through B-9 have been previously described together with the liquid crystal composition according to the embodiment, a detailed description of the compounds will be omitted.

In an exemplary embodiment, the liquid crystal layer 300 may further include a compound RM having a structure represented by formula C-1 below:

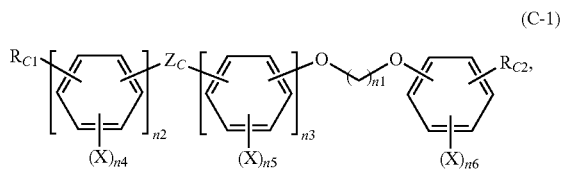

(C-1)

wherein $Z_C$ may be a connector group. In an example, $Z_C$ may be an alkylene group, an alkyleneoxy group, an ether group, or a single bond. In another example, $Z_C$ may be an alkylene group having a carbon number of 1 to 3, an alkyleneoxy group having a carbon number of 1 to 3, an ether group, or a single bond.

In formula C-1, n1 may be an integer of 2 to 4. In addition, in formula C-1, each of n2 and n3 may define a molecular framework structure. For example, each of n2 and n3 may be independently 0 or 1.

In formula C-1, X may be a halogen atom. Examples of the halogen atom may include a fluorine atom, a chlorine atom, a bromine atom, and an iodine atom. In formula C-1, each of n4 through n6 may be independently an integer of 0 to 2. For example, X may be bonded to a benzene group so as to provide high polarity properties to the compound.

In formula C-1, each of $R_{C1}$ and $R_{C2}$ may be a polymerizable reactive group used for polymerization. For example, each of $R_{C1}$ and $R_{C2}$ may be independently

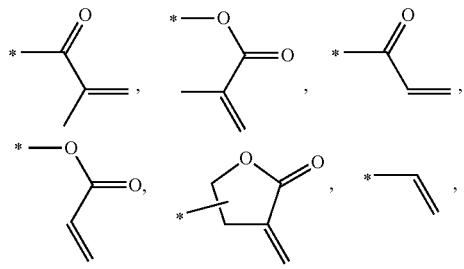

-continued

*≡, or *———≡≡.

The compound RM having the structure represented by formula C-1 may be added in an amount of greater than 0 to about 100 ppm, based on a total weight of the liquid crystal layer 300. If the compound RM having the structure represented by formula C-1 is included in an amount of about 100 ppm or less based on the total weight of the liquid crystal layer 300, the voltage holding ratio and the afterimage defect can be further improved.

Hereinafter, the inventive concept will be described in greater detail with reference to Manufacturing Example and Comparative Example.

Manufacturing Example 1

Compounds having structures represented by formula A-8, A-9 and A-13 were synthesized, and their physical properties were simulated. The simulation results are shown in Table 1.

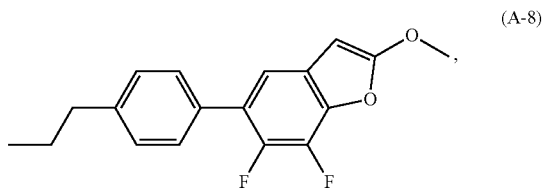

(A-8)

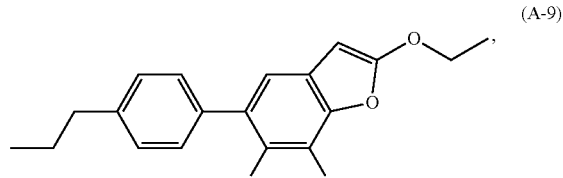

(A-9)

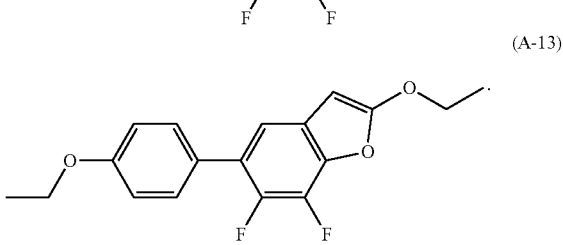

(A-13)

TABLE 1

| Structure | Phase transition temperature (Tni) | Refractive index anisotropy ($\Delta n = n_e - n_o$) | Dielectric anisotropy ($\Delta\varepsilon = \varepsilon_\parallel - \varepsilon_\perp$) | Rotational viscosity (γ1, 20° C.) | Elastic modulus (K33) |
|---|---|---|---|---|---|
| Formula A-8 | 59.9° C. | 0.2440 | −4.87 | 70 | 3.76 mPas |
| Formula A-9 | 69.1° C. | 0.2360 | −5.06 | 91 | 4.98 mPas |
| Formula A-13 | 77.7° C. | 0.2530 | −7.07 | 82 | 3.24 mPas |

Manufacturing Example 2

A liquid crystal composition including the compounds having the structures represented by formulas A-8 and A-13 was manufactured, and its physical properties were simulated. The simulation results are shown in Table 2.

TABLE 2
| Composition | Weight % | Physical properties |
|---|---|---|
| 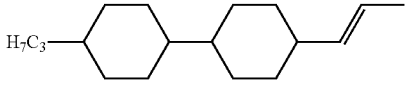 | 15 | Phase transition temperature (Tni, °C.): 76.0<br>Δn(ne − no): 0.108<br>Δε(ε∥ − ε⊥): −3.0<br>Elastic modulus (K33): 12.5<br>Rotational viscosity (γ1, mPas): 104 |
| 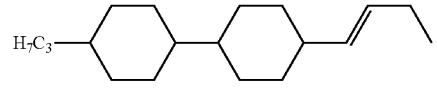 | 10 | |
| 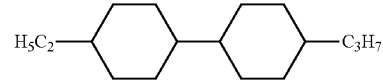 | 9 | |
| 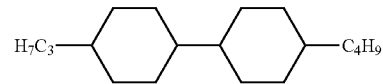 | 8 | |
| 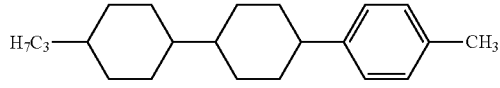 | 3 | |
| 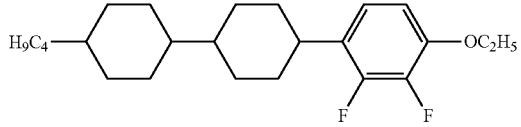 | 10 | |
| 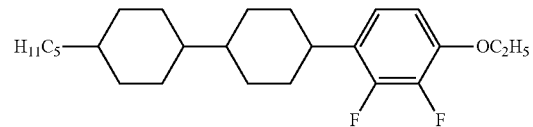 | 8 | |
| 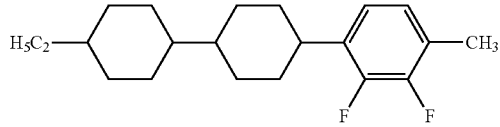 | 7 | |
| 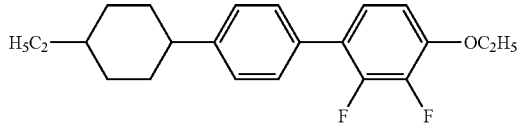 | 10 | |
| 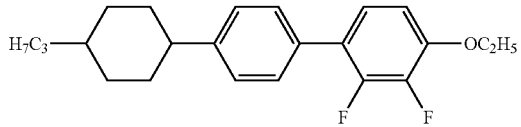 | 8 | |
| Formula A-8 | 7 | |
| Formula A-13 | 5 | |

Comparative Example 1

A liquid crystal composition was manufactured to have the same refractive anisotropy and dielectric anisotropy as the liquid crystal composition according to Manufacturing Example 2, and its physical properties were simulated. The simulation results are shown in Table 3.

Comparative Example 2

A liquid crystal composition was manufactured in the same way as in Manufacturing Example 2 except that a compound having a structure represented by formula A-13' was used instead of the compound having the structure represented by formula A-13. The compound of formula

TABLE 3

| Composition | Weight % | Physical properties |
|---|---|---|
| $H_5C_2$—⬡—⬡—$C_3H_7$ | 22 | Phase transition temperature (Tni, °C.): 75.5<br>Δn(ne − no): 0.108<br>Δε(ε∥ − ε⊥): −3.0<br>Elastic modulus (K33): 13<br>Rotational viscosity (γ1, mPas): 102 |
| $H_7C_3$—⬡—⬡—$C_4H_9$ | 9 | |
| $H_7C_3$—⬡—⬢—$OCH_3$ | 7 | |
| $H_7C_3$—⬡—⬢(F,F)—$OC_2H_5$ | 15 | |
| $H_9C_4$—⬡—⬡—⬢(F,F)—$OC_2H_5$ | 9.5 | |
| $H_{11}C_5$—⬡—⬡—⬢(F,F)—$OC_2H_5$ | 5 | |
| $H_5C_2$—⬡—⬢—⬢(F,F)—$OC_2H_5$ | 9 | |
| $H_7C_3$—⬡—⬢—⬢(F,F)—$OC_2H_5$ | 9 | |
| $H_5C_2$—⬢—⬢(F,F)—⬢—$C_3H_7$ | 7 | |
| $H_5C_2$—⬢—⬢(F,F)—⬢—$C_4H_9$ | 7.5 | |

A-13' was added in an amount of 5 weight %, and its physical properties were simulated. The simulation results are shown in Table 4.

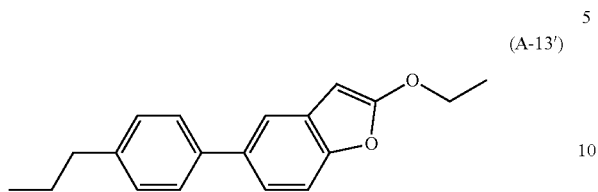

(A-13')

TABLE 4

| Composition | Weight % | Physical properties |
|---|---|---|
| H₇C₃–cyclohexyl–cyclohexyl–CH=CH₂ | 15 | Phase transition temperature (Tni, °C.): 78.0<br>Δn(ne − no): 0.1073<br>Δε(ε∥ − ε⊥): −3.0<br>Elastic modulus (K33): 12.7<br>Rotational viscosity (γ1, mPas): 107 |
| H₇C₃–cyclohexyl–cyclohexyl–CH=CH–C₂H₅ | 10 | |
| H₅C₂–cyclohexyl–cyclohexyl–C₃H₇ | 9 | |
| H₇C₃–cyclohexyl–cyclohexyl–C₄H₉ | 8 | |
| H₇C₃–cyclohexyl–cyclohexyl–phenyl–CH₃ | 3 | |
| H₉C₄–cyclohexyl–cyclohexyl–phenyl(F,F)–OC₂H₅ | 10 | |
| H₁₁C₅–cyclohexyl–cyclohexyl–phenyl(F,F)–OC₂H₅ | 8 | |
| H₅C₂–cyclohexyl–cyclohexyl–phenyl(F,F)–CH₃ | 7 | |
| H₅C₂–cyclohexyl–phenyl–phenyl(F,F)–OC₂H₅ | 10 | |

TABLE 4-continued

| Composition | Weight % | Physical properties |
|---|---|---|
| 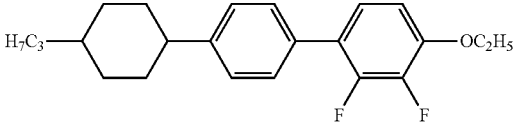 | 8 | |
| Formula A-8 | 7 | |
| Formula A-13' | 5 | |

Referring to Tables 2 and 3, the liquid crystal composition according to Manufacturing Example 2 has superior refractive index anisotropy even without including, for example, a compound having a terphenyl group which is vulnerable (unreliable) to light of a UV wavelength band.

In addition, the liquid crystal composition according to Manufacturing Example 2 has a significantly lower rotational viscosity than the liquid crystal composition according to Comparative Example 1.

Referring to Tables 2 and 4, the liquid crystal composition according to Manufacturing Example 2 has a lower rotational viscosity than the liquid crystal composition according to Comparative Example 2.

According to an embodiment, a liquid crystal composition having both high dielectric anisotropy and low viscosity can be provided. In addition, a display device having a liquid crystal layer including the liquid crystal composition has improved response speed and contrast and a low driving voltage.

However, the effects of the inventive concept are not restricted to the one set forth herein. The above and other effects of the inventive concept will become more apparent to one of daily skill in the art to which the inventive concept pertains by referencing the claims.

While the present invention has been particularly illustrated and described with reference to exemplary embodiments thereof, it will be understood by those of ordinary skill in the art that various changes in form and detail may be made therein without departing from the spirit and scope of the present invention as defined by the following claims. The exemplary embodiments should be considered in a descriptive sense only and not for purposes of limitation.

What is claimed is:

1. A liquid crystal composition comprising a compound having a structure represented by formula A-1:

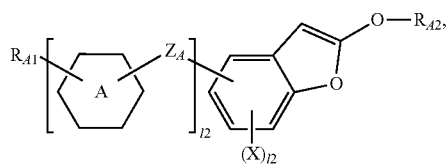

wherein

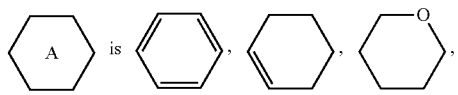

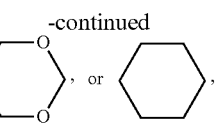

$R_{A1}$ is an alkyl group, an alkoxy group, a cyano group, a halogen atom, or a hydrogen atom, $R_{A2}$ is an alkyl group, a cyano group, a halogen atom, or a hydrogen atom, $Z_A$ is *—O—*, *—COO—*, *—OCO—*, *—CF$_2$O—*, *—OCF$_2$—*, *—CH$_2$O—*, *—OCH$_2$—*, *—SCH$_2$—*, *—CH$_2$S—*, *—C$_2$F$_4$—*, *—CH$_2$CF$_2$—*, *—CF$_2$CH$_2$—*, *—(CH$_2$)$_k$—*, *—CH=CH—*, *—CF=CF—*, *—CH=CF—*, *—CF=CH—*, *—CH=CHCH$_2$O—*, or a single bond, X is a halogen atom, each of l1 and l2 is independently an integer of 0 to 2, and when l1 is 2

and $Z_A$ in a repeating unit defined by l1 are the same or different, k is an integer of 1 to 5, and "*" indicates a point of attachment.

2. The liquid crystal composition of claim 1, wherein the compound having the structure represented by formula A-1 is a compound having a structure represented by formula A-2:

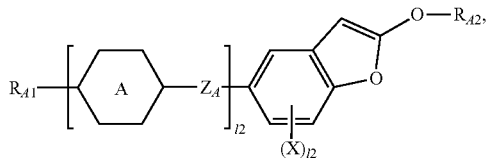

wherein

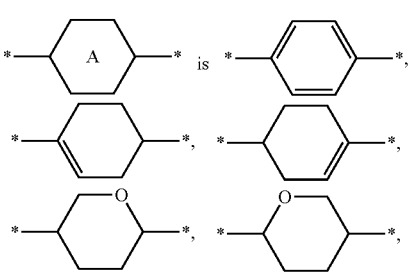

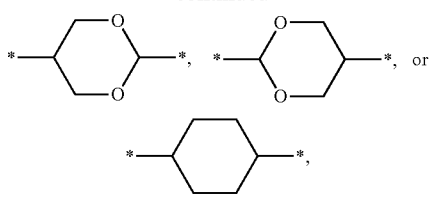

$R_{A1}$ is an alkyl group having a carbon number of 1 to 5, an alkoxy group having a carbon number of 1 to 5, a cyano group, a halogen atom, or a hydrogen atom, $R_{A2}$ is an alkyl group having a carbon number of 1 to 5, a cyano group, a halogen atom, or a hydrogen atom, and $Z_A$, X, l1, and l2 are the same as those in formula A-1.

3. The liquid crystal composition of claim 2, wherein the compound having the structure represented by formula A-2 is a compound having a structure represented by formula A-3, formula A-4, or formula A-5:

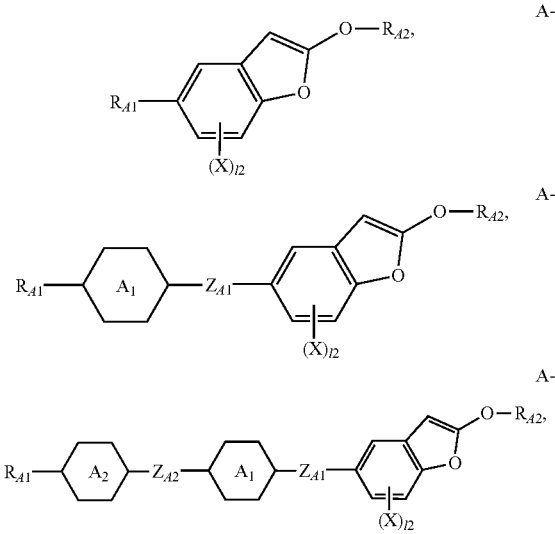

wherein each of

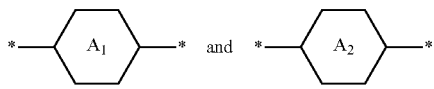

is independently

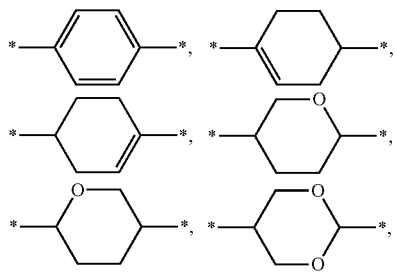

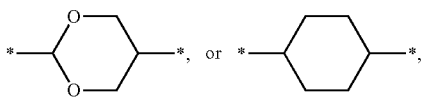

each of $Z_{A1}$ and $Z_{A2}$ is independently *—O—*, *—COO—*, *—OCO—*, *—CF$_2$O—*, *—OCF$_2$—*, *—CH$_2$O—*, *—OCH$_2$—*, *—SCH$_2$—*, *—CH$_2$S—*, *—C$_2$F$_4$—*, *—CH$_2$CF$_2$—*, *—CF$_2$CH$_2$—*, *—(CH$_2$)$_k$—*, *—CH═CH—*, *—CF═CF—*, *—CH═CF—*, *—CF═CH—*, *—C≡C—*, *—CH═CHCH$_2$O—*, or a single bond, $R_{A1}$, $R_{A2}$, X, and l2 are the same as those in formula A-2, and k is an integer of 1 to 5.

4. The liquid crystal composition of claim 3, wherein the compound having the structure represented by formula A-3, formula A-4, or formula A-5 is a compound having a structure represented by any one of formulas A-6 to A-13:

-continued

A-12
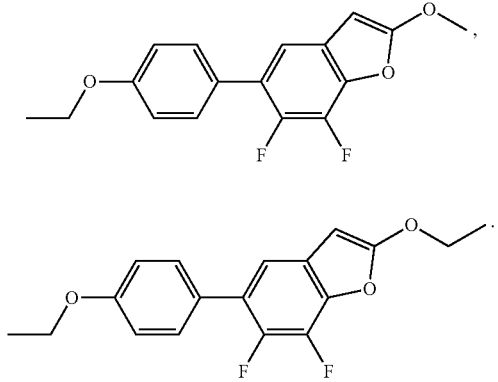

A-13

5. The liquid crystal composition of claim 4, comprising one or more of the compounds having the structures represented by formulas A-6 to A-13.

6. The liquid crystal composition of claim 4, wherein the compound having the structure represented by any one of formulas A-6 to A-13 has a refractive index anisotropy of about 0.230 to about 0.260 and a rotational viscosity at 20° C. of about 70 to about 100 millipascal-seconds.

7. The liquid crystal composition of claim 4, wherein the liquid crystal composition has a refractive index anisotropy of about 0.080 to about 0.120, a dielectric anisotropy of about −5.5 to about −2.8, and a rotational viscosity at 20° C. of about 70 to about 110 millipascal-seconds.

8. The liquid crystal composition of claim 1, further comprising a compound having a structure represented by formula B-1:

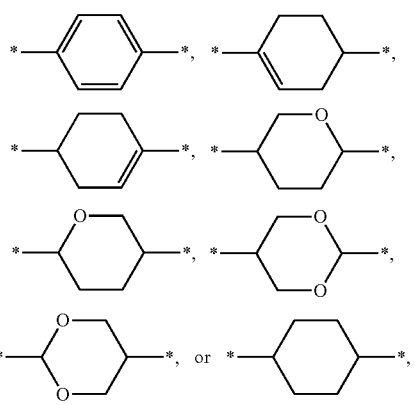

wherein each of

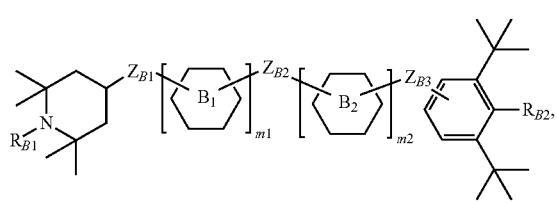

is independently

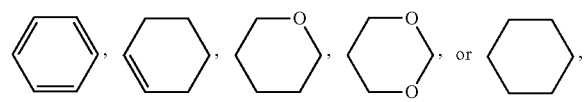

$R_{B1}$ is an alkyl group, an alkoxy group, or a hydrogen atom, $R_{B2}$ is an alkyl group, an alkoxy group, an acetamide group, a hydroxyl group, or a hydrogen atom, each of $Z_{B1}$, $Z_{B2}$, and $Z_{B3}$ is independently alkylene group having a carbon number of 1 to 5, an alkenylene group having a carbon number of 2 to 3, *—O—*, *—COO—*, *—OCO—*, *—CF$_2$O—*, *—OCF$_2$—*, a single bond, or a double bond, and each of m1 and m2 is independently 0 or 1.

9. The liquid crystal composition of claim 8, wherein the compound having the structure represented by formula B-1 is a compound having a structure represented by formula B-2:

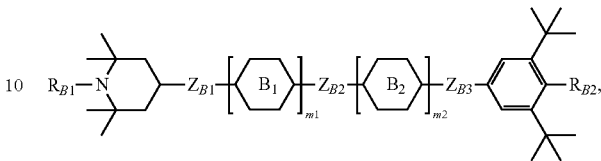

wherein each of

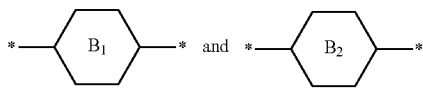

is independently

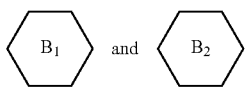

$R_{B1}$ is an alkyl group having a carbon number of 1 to 5, an alkoxy group having a carbon number of 1 to 5, or a hydrogen atom, $R_{B2}$ is an alkyl group having a carbon number of 1 to 4, an alkoxy group having a carbon number of 1 to 4, an acetamide group, a hydroxyl group or a hydrogen atom, and $Z_{B1}$, $Z_{B2}$, $Z_{B3}$, m1, and m2 are the same as those in formula B-1.

10. The liquid crystal composition of claim 9, wherein the compound having the structure represented by formula B-2 is a compound having a structure represented by formula B-3, formula B-4, or formula B-5:

B-3
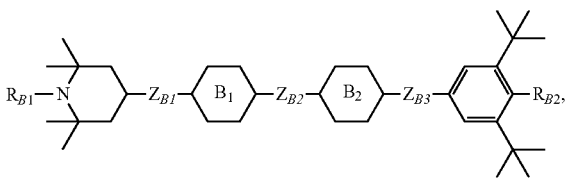

-continued

B-4
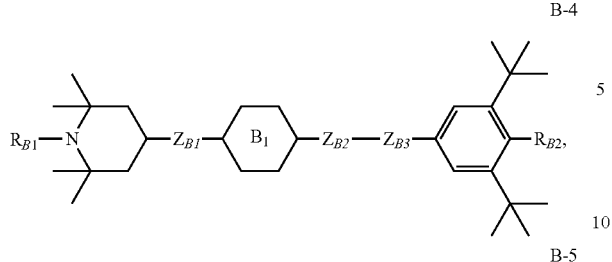

B-5
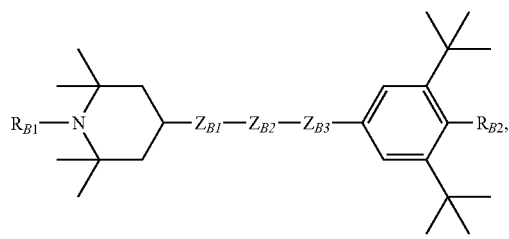

wherein

$R_{B1}$, $R_{B2}$, $Z_{B1}$, $Z_{B2}$, and $Z_{B3}$ are the same as those in formula B-2.

11. The liquid crystal composition of claim 10, wherein the compound having the structure represented by formula B-3, formula B-4, or formula B-5 is a compound having a structure represented by any one of formulas B-6 to B-9:

B-6
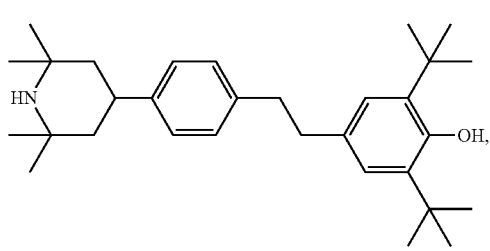

B-7
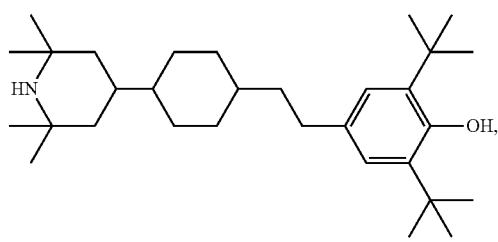

B-8
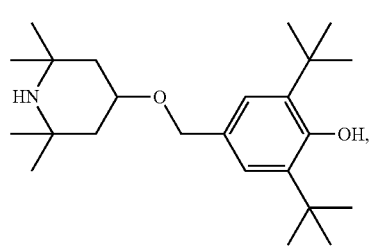

-continued

B-9
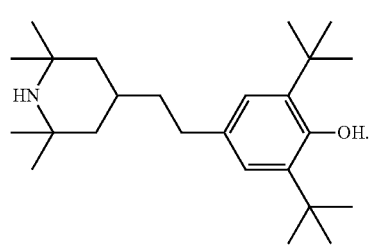

12. The liquid crystal composition of claim 8, further comprising a compound having a structure represented by formula C-1:

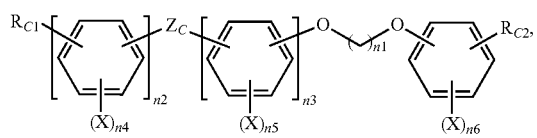

wherein each of $R_{C1}$ and $R_{C2}$ is independently

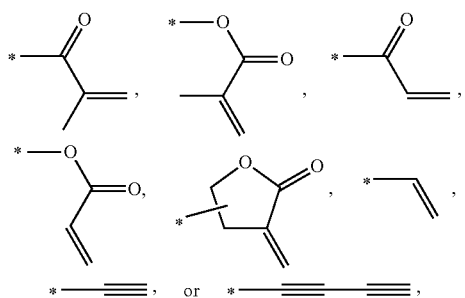

$Z_C$ is an alkylene group, an alkyleneoxy group, an ether group, or a single bond, X is a halogen atom, n1 is an integer of 2 to 4, each of n2 and n3 is independently 0 or 1, and each of n4 to n6 is independently an integer of 0 to 2.

13. The liquid crystal composition of claim 12, wherein the compound having the structure represented by formula C-1 is a compound having a structure represented by formula C-2:

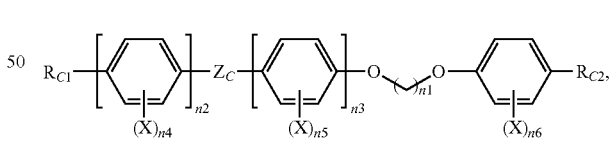

wherein $R_{C1}$, $R_{C2}$, $Z_C$, X, and n1 to n6 are the same as those in formula C-1.

14. The liquid crystal composition of claim 13, wherein the compound having the structure represented by formula C-2 is a compound having a structure represented by formula C-3 or formula C-4:

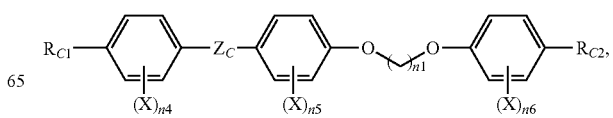

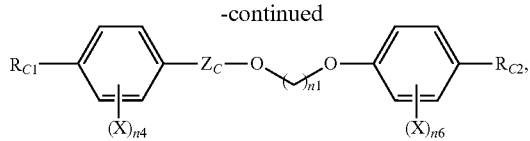

wherein $R_{C1}$, $R_{C2}$, $Z_C$, X, n1, n4, and n6 are the same as those in formula C-1.

15. The liquid crystal composition of claim 14, wherein the compound having the structure represented by formula C-3 or formula C-4 is a compound having a structure represented by any one of formulas C-5 to C-8:

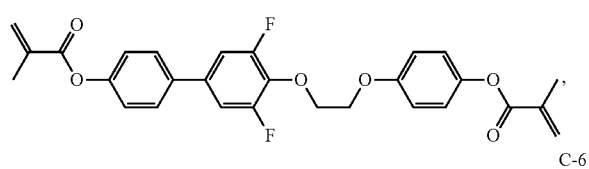

C-5

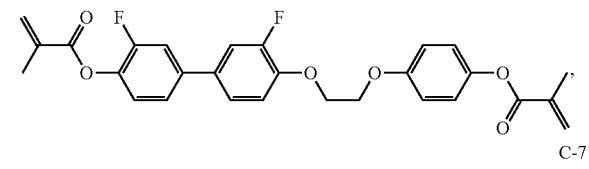

C-6

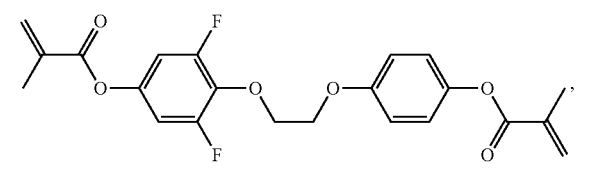

C-7

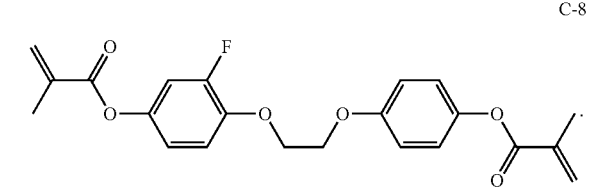

C-8

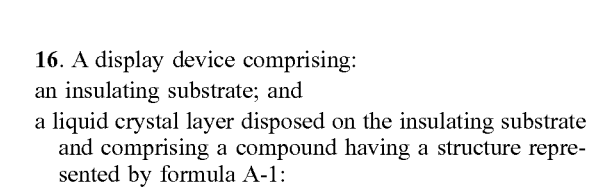

16. A display device comprising:
an insulating substrate; and
a liquid crystal layer disposed on the insulating substrate and comprising a compound having a structure represented by formula A-1:

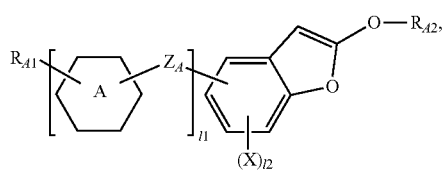

wherein

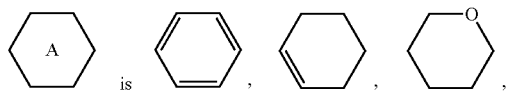

is

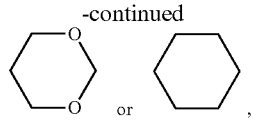

or $R_{A1}$ is an alkyl group, an alkoxy group, a cyano group, a halogen atom, or a hydrogen atom, $R_{A2}$ is an alkyl group, a cyano group, a halogen atom or a hydrogen atom, $Z_A$ is *—O—*, *—COO—*, *—OCO—*, *—CF$_2$O—*, *—OCF$_2$—*, *—CH$_2$O—*, *—OCH$_2$—*, *—SCH$_2$—*, *—CH$_2$S—*, *—C$_2$F$_4$—*, *—CH$_2$CF$_2$—*, *—CF$_2$CH$_2$—*, *—(CH$_2$)$_k$—*, *—CH=CH—*, *—CF=CF—*, *—CH=CF—*, *—CF=CH—*, *—C≡C—*, *—CH=CHCH$_2$O—*, or a single bond, X is a halogen atom, l1 is an integer of 0 to 2, l2 is an integer of 0 to 3, and when l1 is 2

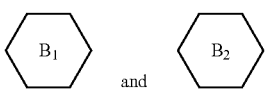

and $Z_A$ in a repeating unit defined by l1 are the same or different, k is an integer of 1 to 5, and "*" indicates a point of attachment.

17. The display device of claim 16, wherein the liquid crystal layer further comprises a compound having a structure represented by formula B-1:

(B-1)

wherein each of and is independently

, , , , or

, $R_{B1}$ is an alkyl group, an alkoxy group, or a hydrogen atom, $R_{B2}$ is an alkyl group, an alkoxy group, an acetamide group, a hydroxyl group, or a hydrogen atom, each of $Z_{B1}$, $Z_{B2}$ and $Z_{B3}$ is independently an alkylene group having a carbon number of 1 to 5, an alkenylene group having a carbon number of 2 to 3, *—O—*, *—COO—*, *—OCO—*,

*—CF₂O—*, *—OCF₂—*, a single bond, or a double bond, and each of m1 and m2 is independently 0 or 1.

18. The display device of claim 17, further comprising an alignment layer disposed between the insulating substrate and the liquid crystal layer, wherein the alignment layer comprises a main alignment layer, which comprises a main chain having an imide group as a repeating unit, and an alignment stabilization layer comprising a crosslinked polymer comprising a compound having a structure represented by formula C-1:

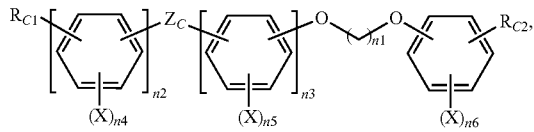

wherein each of $R_{C1}$ and $R_{C2}$ is independently

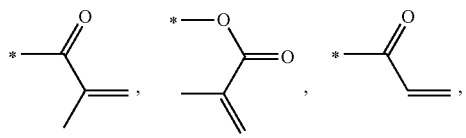

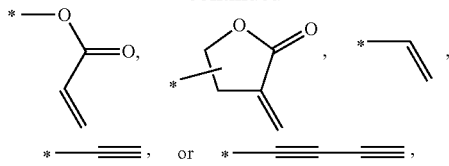

$Z_C$ is an alkylene group, an alkyleneoxy group, an ether group or a single bond, X is a halogen atom, n1 is an integer of 2 to 4, each of n2 and n3 is independently 0 or 1, and each of n4 to n6 is independently an integer of 0 to 2.

19. The display device of claim 18, wherein the liquid crystal layer further comprises the compound having the structure represented by formula C-1, wherein the compound having the structure represented by formula C-1 is present in an amount of about 100 ppm or less based on a total weight of the liquid crystal layer.

20. The display device of claim 19, further comprising:
a first electrode disposed between the insulating substrate and the alignment layer; and
a second electrode facing the first electrode, and the liquid crystal layer disposed between the first electrode and the second electrode.

* * * * *